(12) United States Patent
Bowditch et al.

(10) Patent No.: US 8,517,017 B2
(45) Date of Patent: Aug. 27, 2013

(54) SELF-CONTAINED, INTERMITTENT POSITIVE AIRWAY PRESSURE SYSTEMS AND METHODS FOR TREATING SLEEP APNEA, SNORING, AND OTHER RESPIRATORY DISORDERS

(75) Inventors: Nathaniel L. Bowditch, Menlo Park, CA (US); Thomas G. Goff, Mountain View, CA (US); Tarmigan Casebolt, San Francisco, CA (US)

(73) Assignee: Hancock Medical, Inc., Mountain View, CA (US)

( * ) Notice: Subject to any disclaimer, the term of this patent is extended or adjusted under 35 U.S.C. 154(b) by 701 days.

(21) Appl. No.: 12/655,829

(22) Filed: Jan. 8, 2010

(65) Prior Publication Data
US 2010/0170513 A1     Jul. 8, 2010

Related U.S. Application Data

(60) Provisional application No. 61/143,371, filed on Jan. 8, 2009.

(51) Int. Cl.
*A61M 16/00* (2006.01)

(52) U.S. Cl.
USPC ............................. 128/204.23; 128/204.18

(58) Field of Classification Search
USPC ...................................... 128/204.23, 204.18
See application file for complete search history.

(56) References Cited

U.S. PATENT DOCUMENTS

| | | | |
|---|---|---|---|
| 3,649,964 A | 3/1972 | Schoelz et al. | |
| 3,721,233 A | 3/1973 | Montgomery et al. | |
| 3,736,927 A | 6/1973 | Misaqi | |
| 3,822,698 A | 7/1974 | Guy | |
| 3,881,198 A | 5/1975 | Waters | |
| 3,998,213 A | 12/1976 | Price | |
| 4,019,508 A | 4/1977 | Der Estephanian et al. | |
| 4,233,972 A | 11/1980 | Hauff et al. | |
| 4,297,999 A | 11/1981 | Kitrell | |
| 4,381,267 A | 4/1983 | Jackson | |

(Continued)

FOREIGN PATENT DOCUMENTS

| | | |
|---|---|---|
| EP | 0 558 147 A | 9/1993 |
| EP | 1 655 052 A2 | 5/2006 |

(Continued)

OTHER PUBLICATIONS

International Preliminary Report on Patentability; PCT/US10/00046; Jan. 27, 2011.

(Continued)

*Primary Examiner* — Laura Bouchelle
(74) *Attorney, Agent, or Firm* — Morrison & Foerster LLP

(57) ABSTRACT

Systems and methods provide a self-contained, intermittent positive airway pressure system for treating sleep apnea, snoring, and other respiratory disorders. The systems and methods provide an air flow director that can be worn in or over the nose of the individual in communication with an upper airway. The systems and methods provide an airflow regulation assembly that can also be worn in its entirety by the individual in communication with the air flow director. The airflow regulation assembly includes a source of positive pressure. The airflow regulation assembly intermittently operates the source of positive pressure to increase positive air pressure in the air flow director sufficient to resist tissue collapse in the upper airway during only a portion of the respiratory cycle less than the entire respiratory cycle.

28 Claims, 18 Drawing Sheets

(56) References Cited

U.S. PATENT DOCUMENTS

| | | |
|---|---|---|
| 4,430,995 A | 2/1984 | Hilton |
| 4,549,542 A | 10/1985 | Chien |
| 4,590,951 A | 5/1986 | O'Connor |
| 4,644,947 A | 2/1987 | Whitwam et al. |
| 4,765,316 A | 8/1988 | Marshall |
| 4,782,832 A | 11/1988 | Trimble et al. |
| 4,802,485 A | 2/1989 | Bowers et al. |
| 4,829,998 A | 5/1989 | Jackson |
| 4,836,219 A | 6/1989 | Hobson et al. |
| 4,944,310 A | 7/1990 | Sullivan |
| 5,035,239 A | 7/1991 | Edwards |
| 5,046,492 A | 9/1991 | Stackhouse et al. |
| 5,054,480 A | 10/1991 | Bare et al. |
| 5,054,484 A | 10/1991 | Hebeler, Jr. |
| 5,104,430 A | 4/1992 | Her-Mou |
| 5,113,853 A | 5/1992 | Dickey |
| 5,154,168 A | 10/1992 | Schlobohm |
| 5,303,701 A | 4/1994 | Heins et al. |
| 5,318,020 A | 6/1994 | Schegerin |
| 5,349,946 A | 9/1994 | McComb |
| 5,353,788 A | 10/1994 | Miles |
| 5,372,130 A | 12/1994 | Stern et al. |
| 5,394,870 A | 3/1995 | Johansson |
| 5,461,934 A | 10/1995 | Budd |
| 5,485,851 A | 1/1996 | Erickson |
| 5,517,986 A | 5/1996 | Starr et al. |
| 5,533,500 A | 7/1996 | Her-Mou |
| RE35,339 E | 10/1996 | Rapoport |
| 5,564,124 A | 10/1996 | Elsherif et al. |
| 5,577,496 A | 11/1996 | Blackwood et al. |
| 5,657,752 A | 8/1997 | Landis et al. |
| 5,769,071 A | 6/1998 | Turnbull |
| 5,928,189 A | 7/1999 | Phillips et al. |
| 5,937,855 A | 8/1999 | Zdrojkowski et al. |
| 5,950,621 A | 9/1999 | Klockseth et al. |
| 5,954,050 A | 9/1999 | Christopher |
| 5,961,447 A | 10/1999 | Raviv et al. |
| 6,050,262 A | 4/2000 | Jay |
| 6,122,773 A | 9/2000 | Katz |
| 6,179,586 B1 | 1/2001 | Herb et al. |
| 6,213,119 B1 | 4/2001 | Brydon et al. |
| 6,349,724 B1 | 2/2002 | Burton et al. |
| 6,393,617 B1 | 5/2002 | Paris et al. |
| 6,397,845 B1 | 6/2002 | Burton |
| 6,431,171 B1 | 8/2002 | Burton |
| 6,435,180 B1 | 8/2002 | Hewson et al. |
| 6,435,184 B1 | 8/2002 | Ho |
| 6,513,526 B2 | 2/2003 | Kwok et al. |
| 6,532,960 B1 | 3/2003 | Yurko |
| 6,561,190 B1 | 5/2003 | Kwok |
| 6,561,191 B1 | 5/2003 | Kwok |
| 6,622,311 B2 | 9/2003 | Diaz et al. |
| 6,634,864 B1 | 10/2003 | Young et al. |
| 6,694,978 B1 | 2/2004 | Bennarsten |
| 6,705,314 B1 | 3/2004 | O'Dea |
| 6,709,405 B2 | 3/2004 | Jonson |
| 6,711,748 B2 | 3/2004 | Paris et al. |
| 6,752,146 B1 | 6/2004 | Altshuler et al. |
| 6,772,760 B2 | 8/2004 | Frater et al. |
| 6,772,762 B2 | 8/2004 | Piesinger |
| 6,854,465 B2 | 2/2005 | Bordewick et al. |
| 6,881,192 B1 | 4/2005 | Park |
| 6,889,691 B2 | 5/2005 | Eklund et al. |
| 6,895,959 B2 | 5/2005 | Lukas |
| 6,920,877 B2 | 7/2005 | Remmers et al. |
| 7,019,652 B2 | 3/2006 | Richardson |
| 7,069,932 B2 | 7/2006 | Eaton et al. |
| 7,089,941 B2 | 8/2006 | Bordewick et al. |
| 7,096,864 B1 | 8/2006 | Mayer et al. |
| 7,118,608 B2 | 10/2006 | Lovell |
| 7,128,069 B2 | 10/2006 | Farrugia et al. |
| 7,156,090 B2 | 1/2007 | Nomori |
| 7,178,525 B2 | 2/2007 | Matula, Jr. et al. |
| 7,195,014 B2 | 3/2007 | Hoffman |
| 7,200,873 B2 | 4/2007 | Klotz et al. |
| 7,204,250 B1 | 4/2007 | Burton |
| 7,255,103 B2 | 8/2007 | Bassin |
| 7,357,136 B2 | 4/2008 | Ho et al. |
| 7,471,290 B2 | 12/2008 | Wang et al. |
| 7,487,778 B2 | 2/2009 | Freitag |
| 7,516,743 B2 | 4/2009 | Hoffman |
| 7,575,005 B2 | 8/2009 | Mumford et al. |
| 7,588,033 B2 | 9/2009 | Wondka |
| 7,664,546 B2 | 2/2010 | Hartley et al. |
| 7,681,575 B2 | 3/2010 | Wixey et al. |
| 7,766,841 B2 | 8/2010 | Yamamoto et al. |
| 7,810,496 B2 | 10/2010 | Estes et al. |
| 7,901,361 B2 | 3/2011 | Rapoport et al. |
| 7,913,692 B2 | 3/2011 | Kwok |
| 7,934,500 B2 | 5/2011 | Madaus et al. |
| 7,942,824 B1 | 5/2011 | Kayyali et al. |
| 8,020,557 B2 | 9/2011 | Bordewick et al. |
| 8,069,852 B2 | 12/2011 | Burton et al. |
| 2002/0104541 A1 | 8/2002 | Bibi et al. |
| 2003/0062045 A1 | 4/2003 | Woodring et al. |
| 2003/0079749 A1 | 5/2003 | Strickland et al. |
| 2003/0172930 A1 | 9/2003 | Kullik et al. |
| 2004/0079373 A1 | 4/2004 | Mukaiyama et al. |
| 2004/0163648 A1 | 8/2004 | Burton |
| 2004/0226562 A1 | 11/2004 | Bordewick |
| 2005/0005937 A1* | 1/2005 | Farrugia et al. .......... 128/204.18 |
| 2005/0034724 A1 | 2/2005 | O'Dea |
| 2005/0068639 A1 | 3/2005 | Pierrat et al. |
| 2005/0133039 A1 | 6/2005 | Wood |
| 2006/0081250 A1 | 4/2006 | Bordewick et al. |
| 2006/0096596 A1* | 5/2006 | Occhialini et al. ....... 128/204.18 |
| 2006/0150973 A1 | 7/2006 | Chalvignac |
| 2006/0213516 A1 | 9/2006 | Hoffman |
| 2006/0231097 A1 | 10/2006 | Dougherty et al. |
| 2006/0231102 A1 | 10/2006 | Bordewick et al. |
| 2006/0237013 A1 | 10/2006 | Kwok |
| 2006/0272641 A1 | 12/2006 | Madaus et al. |
| 2007/0000493 A1 | 1/2007 | Cox |
| 2007/0089743 A1 | 4/2007 | Hoffman |
| 2007/0240716 A1 | 10/2007 | Marx |
| 2007/0246045 A1 | 10/2007 | Hoffman |
| 2007/0247009 A1 | 10/2007 | Hoffman et al. |
| 2007/0251527 A1 | 11/2007 | Sleeper |
| 2007/0277825 A1 | 12/2007 | Bordewick et al. |
| 2008/0006275 A1 | 1/2008 | Nickelson et al. |
| 2008/0053451 A1 | 3/2008 | Bordewick et al. |
| 2008/0185002 A1 | 8/2008 | Berthon-Jones et al. |
| 2008/0216831 A1 | 9/2008 | McGinnis et al. |
| 2008/0304986 A1 | 12/2008 | Kenyon et al. |
| 2009/0078255 A1 | 3/2009 | Bowman et al. |
| 2009/0078258 A1 | 3/2009 | Bowman et al. |
| 2009/0194101 A1 | 8/2009 | Kenyon et al. |
| 2010/0108070 A1 | 5/2010 | Kwok |
| 2010/0170513 A1 | 7/2010 | Bowditch et al. |
| 2010/0180895 A1 | 7/2010 | Kwok et al. |
| 2010/0191076 A1 | 7/2010 | Lewicke et al. |
| 2010/0240982 A1 | 9/2010 | Westbrook et al. |
| 2011/0056489 A1 | 3/2011 | Slaker et al. |
| 2011/0100366 A1 | 5/2011 | Chou |
| 2011/0105915 A1 | 5/2011 | Bauer et al. |
| 2011/0192400 A9 | 8/2011 | Burton et al. |
| 2012/0000463 A1 | 1/2012 | Bordewick et al. |

FOREIGN PATENT DOCUMENTS

| | | |
|---|---|---|
| EP | 1 655 052 A3 | 5/2006 |
| WO | WO-91/19527 A1 | 12/1991 |
| WO | WO-99/013931 A1 | 3/1999 |
| WO | WO-99/21602 A1 | 5/1999 |
| WO | WO-02/085417 A2 | 10/2002 |
| WO | WO-02/085417 A3 | 10/2002 |
| WO | WO-2006/041120 C1 | 4/2006 |
| WO | WO-2006/044120 A2 | 4/2006 |
| WO | WO-2006/044120 A3 | 4/2006 |
| WO | WO-2007/149446 A2 | 12/2007 |
| WO | WO-2007/149446 A3 | 12/2007 |

OTHER PUBLICATIONS

Hofsoy, D. A. et al. (Jun. 2009). "Monitoring and Therapy of Sleep Related Breathing Disorders," IEEE, Wearable Micro and Nano Technologies for Personalized Health (pHealth), 2009, 6$^{th}$ Internatioanl Workshop, pp. 41-44.

Penzel, T. et al. (2001). "Effect of Sleep Position and Sleep Stage on the Collapsibility of the Upper Airways in Patients with Sleep Apnea," Sleep 24(1):90-95.

U.S. Appl. No. 60/494,119, filed Aug. 12, 2003, by Gunaratnam.

* cited by examiner

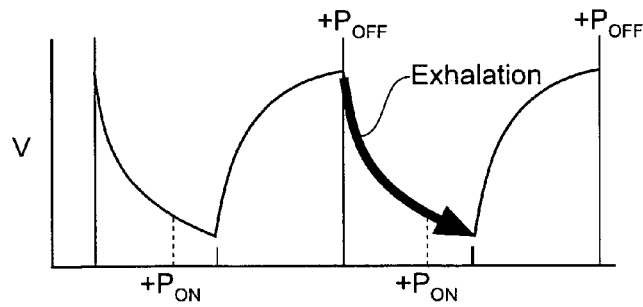
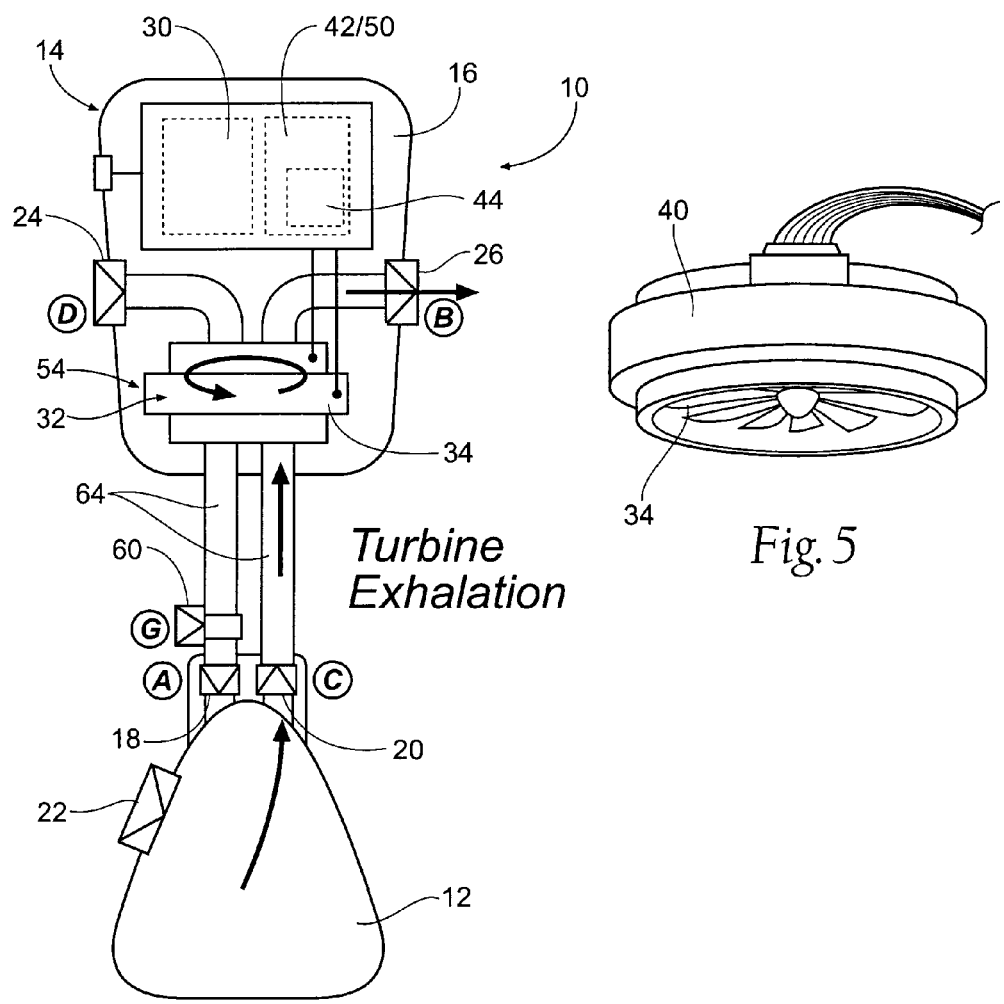
Fig. 4B
Fig. 5

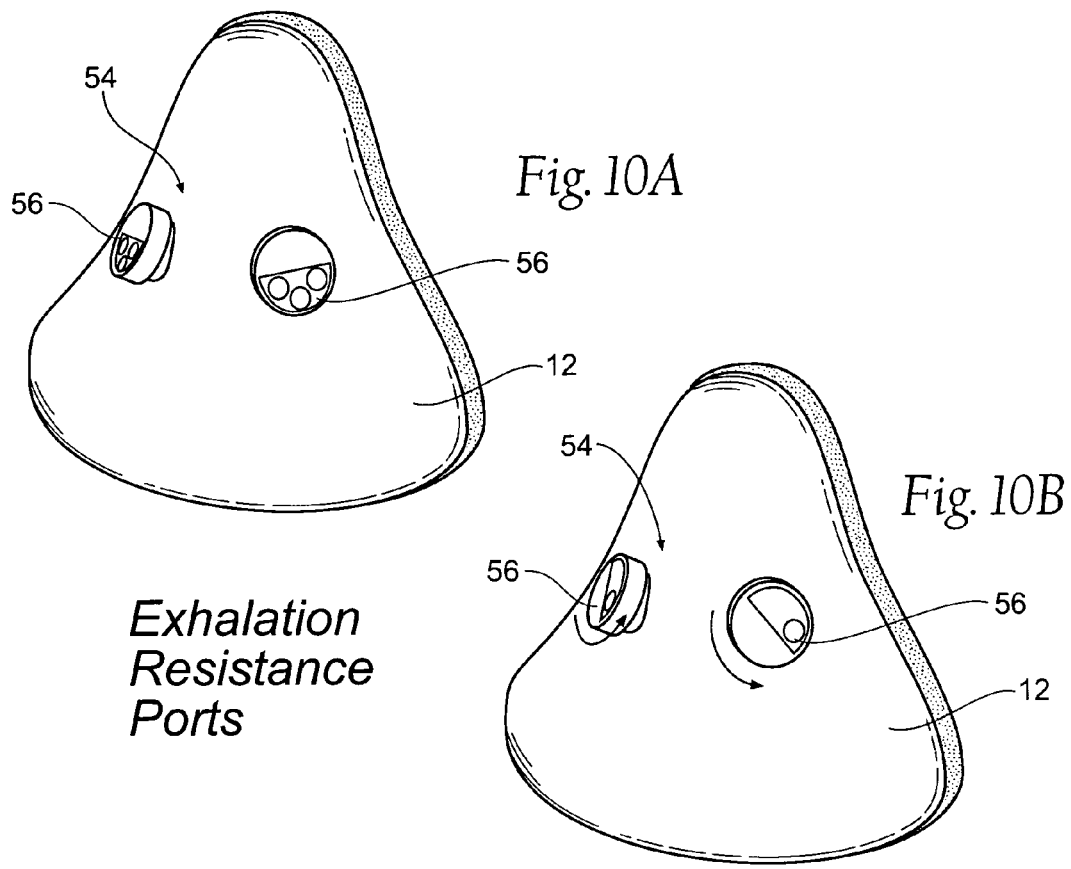
Fig. 10A
Fig. 10B
Exhalation Resistance Ports
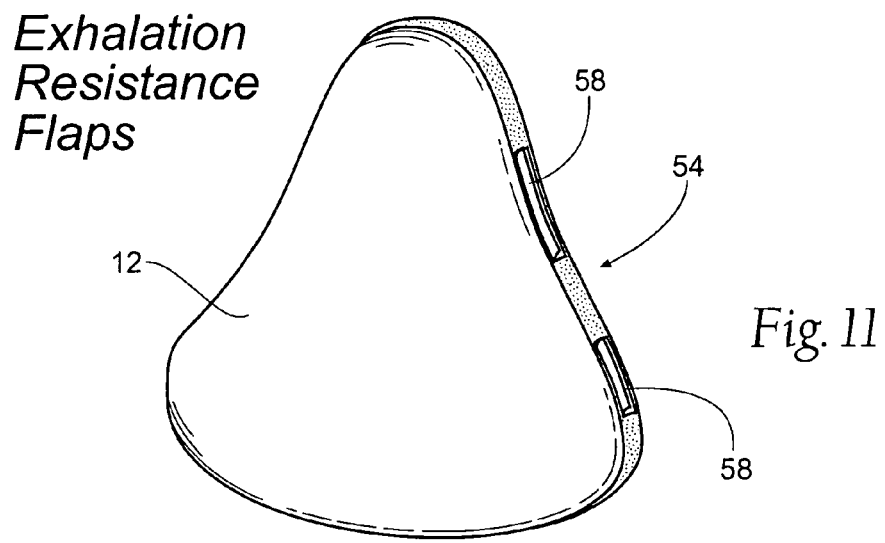
Exhalation Resistance Flaps
Fig. 11

SELF-CONTAINED, INTERMITTENT POSITIVE AIRWAY PRESSURE SYSTEMS AND METHODS FOR TREATING SLEEP APNEA, SNORING, AND OTHER RESPIRATORY DISORDERS

RELATED APPLICATION

This application claims the benefit of U.S. Provisional Patent Application Ser. No. 61/143,371 filed 8 Jan. 2009, and entitled "DEVICES AND METHODS FOR TREATING RESPIRATORY DISORDERS" which is incorporated herein by reference.

FIELD OF THE INVENTION

The invention generally relates to respiration aids to prevent partial or complete airway blockage during sleep, or other respiratory disorders. The invention also generally relates to positive airway pressure systems and methods.

BACKGROUND OF THE INVENTION

During sleep, all muscles, including those of the upper airway, lose tone and relax. Obstructive Sleep Apnea (OSA) occurs when tissue blocks the upper airway during sleep. This will cause a drop in blood oxygen and a rise in blood carbon dioxide. The brain will sense these changes, and awaken the person enough to restore muscle tone to the structures of the upper airway, and the airway will reopen.

The severity of OSA is determined by the number of blockages per hour of sleep, also called the apnea-hypopnea index (AHI). These include complete blockages (apneas) and partial blockages (hypopneas). The severity of OSA, as determined by a sleep study, is classified as follows:

| Severity | Blockages per Hour (AHI) |
| --- | --- |
| Mild | 5-15 |
| Moderate | 15-30 |
| Severe | 30+ |

OSA disrupts restorative sleep. Chronic fatigue has long been recognized as the hallmark of OSA. But more recently, large clinical studies have shown a strong link between OSA and stroke and death. This link is independent of other risk factors for cardiovascular disease such as hypertension, obesity, high cholesterol, smoking and diabetes.

Current Therapies

Several structures can cause blockage of the upper airway: the tongue, the soft palate, the lateral walls of the pharynx, the tonsils and the epiglottis. In most patients, the blockage is caused by a combination of these anatomical structures.

Many procedures and devices have been used to stabilize, modify or remove tissue in the airway to treat OSA. In uvulopalatopharygoplasty (UPPP), the uvula, part of the soft palate and the tonsils are removed. The Repose stitch is used to tie the tongue to the mandible to prevent its posterior movement. Oral appliances move the mandible forward (very slightly) to create more space in the airway.

None of these approaches has achieved much more than a 50% success rate, with success defined as a 50% decrease in AHI to a score below 20. The limited success of these approaches likely stems from the fact that they don't address all anatomical sources of a blockage.

The most widely used therapy for OSA is Continuous Positive Airway Pressure, or CPAP. A CPAP system consists of three parts: an airtight mask fitting in or over the nose or nose and mouth, an air pressurizing console and a tube connecting the two. The mask contains one or more holes. CPAP works by pressurizing the upper airway throughout the breathing cycle, essentially inflating the airway to keep it open. CPAP thus maintains a pneumatic splint throughout the respiratory cycle.

Unlike interventions that treat specific blockages, CPAP addresses all potential blockage sites. The success rate in patients exceeds 80%, and its cure rate (decreasing AHI below 5) is close to 50%. The drawback to CPAP is poor patient compliance. Roughly half of all patients who try CPAP are unable to sleep with it. Patients dislike several aspects of CPAP including: having to wear a mask, being tethered to a pressurizing console, the noise of the console, traveling with a bulky device, and a loss of personal space in the bed.

There is good evidence that an effective pneumatic splint can be achieved within part of the respiratory cycle by producing a partial blockage in the nose or mouth, thus slowing the release of air during expiration. The simplest method, pursing of the lips, has been shown to open the upper airway and improve breathing in emphysema patients.

Doshi et al. (US Patent Application 2006/0150978) describe removable nasal devices that provide considerably more resistance during exhalation than during inhalation. Early results with this type of device are promising, although the results are not as good as those achieved with CPAP. See, Colrain I M, Turlington S. The use of a nasal resistance valve to treat sleep disordered breathing. SLEEP abstract 2008; Rosenthal L, Dolan D C, Massie C A, Kram J. A novel expiratory pressure device to obstructive sleep apnea. SLEEP abstract 2008; Massie C, Rosenthal L, Kram J. Acceptance and Adherence of a novel device in the treatment of sleep apnea. SLEEP abstract 2008.

The drawback to the devices described by Doshi is that increased airway pressure (the "Pneumatic splint") is only achieved during exhalation: there is no increased pressure during inhalation. Additionally, the nasal device described by Doshi cannot be used beneficially by mouth breathers, or patients who become mouth breathers when resistance is added to the nasal passages.

Several devices providing a proximal blockage and covering both the nose and mouth have been described. Oren (U.S. Pat. No. 5,649,533) describes a mask covering the nose or nose and mouth which has two valves. The first valve opens during inhalation, that is when external pressure exceeds pressure within the mask. The second valve opens when pressure within the mask exceeds pressure outside the mask within a certain range, but which will close when pressure within the mask exceeds atmospheric pressure by a predetermined amount (as would be achieved near the end of expiration). This device thus relies on complete closure of all valves near the end of expiration to achieve a pneumatic splint. The drawback to the system is that it does not allow the patients to complete expiration before initiating inspiration.

Bibi (U.S. Pat. No. 6,371,112) describes a system that contains both a mouthpiece and a nasal mask. This fairly complex system uses an inflatable body within the mouthpiece to maintain elevated pressure within the airway throughout the respiratory cycle. The drawback to the system is the requirement for a sizable device within the mouth.

SUMMARY OF THE INVENTION

One aspect of the invention provides systems and methods to aid respiration of an individual during a respiratory cycle having an inhalation phase and an exhalation phase. The systems and methods provide an air flow director sized and configured to be worn in or over the nose of the individual in communication with an upper airway. The systems and methods provide an airflow regulation assembly sized and configured to be worn in its entirety by the individual in communication with the air flow director. The airflow regulation assembly includes a source of positive pressure. The systems and methods operate the airflow regulation assembly in a first mode to regulate the supply of air to the air flow director during the inhalation phase of the respiratory cycle. The systems and methods operate the airflow regulation assembly in a second mode to regulate the exhaust of air from the air flow director during the exhalation phase of the respiratory cycle. The systems and methods intermittently operate the source of positive pressure to increase positive air pressure in the air flow director sufficient to resist tissue collapse in the upper airway during only a portion of the respiratory cycle less than the entire respiratory cycle.

The source of positive pressure can comprise, e.g., a turbine, a blower, and/or an air reservoir.

In one illustrative embodiment, the airflow director comprises a mask that fits over the nose or nose and mouth, and which may have portions within the nostrils. The source of pressurized air in the airflow regulation assembly provides increased air pressure within the mask and upper airway sufficient to resist tissue collapse in the upper airway during at least a portion of exhalation and/or inhalation without a separate pressurizing console. Airflow may also be restricted upon exhalation by one or more exhaust holes with limited cross-sectional area or turbines through which exhaled air may pass, to increase pressure in mask and inflate the upper airway during exhalation.

In another representative embodiment, as the air moves through the turbine, the turbine can serve to store energy. At the completion of exhalation (or at some point before or after the completion of exhalation), the turbine or a blower can draw upon this stored energy to blow positive air pressure into the mask. This may occur throughout inhalation, or during a portion of inhalation, or prior to the start of inhalation. Alternatively, some or all of the energy required to blow positive air pressure into the mask during inhalation can be provided by an energy source that is not replenished by the energy created by exhalation. The energy may be provided by a battery which is recharged daily, or a disposable battery or batteries, or a capacitor. The battery is desirably part of the airflow regulation assembly.

BRIEF DESCRIPTION OF THE DRAWINGS

FIGS. 4A and 4B are schematic views a self-contained, intermittent positive airway pressure system as shown in FIGS. 1A to 1D or FIGS. 2A and 2B, which includes a positive pressure source comprising a turbine 34, FIG. 4A showing the system during inhalation and FIG. 4B showing the system during exhalation.

FIG. 5 is a perspective view of an illustrative embodiment of a turbine that can be used in the system shown in FIGS. 4A and 4B.

FIGS. 10A and 10B are perspective views showing representative embodiments of a mask that can be incorporated into a self-contained, intermittent positive airway pressure system as shown in FIGS. 1A to 1D or FIGS. 2A and 2B, the mask having airflow resistance ports that resist the passage of air during exhalation.

FIG. 11 is a perspective view of a representative embodiment of a mask that can be incorporated into a self-contained, intermittent positive airway pressure system as shown in FIGS. 1A to 1D or FIGS. 2A and 2B, the mask having exhalation resistance flaps that resist the passage of air during exhalation.

DESCRIPTION OF THE PREFERRED EMBODIMENTS

Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention, which is defined by the claims.

I. Overview

Figure 1A:
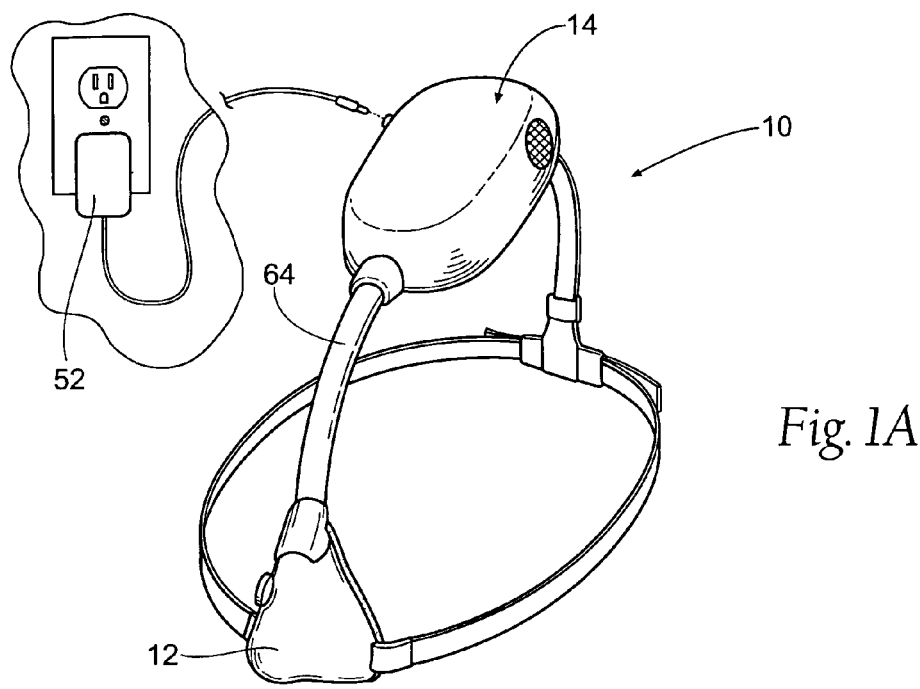
FIGS. 1A to 1D are perspective views of illustrative embodiments of a self-contained, intermittent positive airway pressure system for treating sleep apnea, snoring, and other respiratory disorders.
Figure 1B:
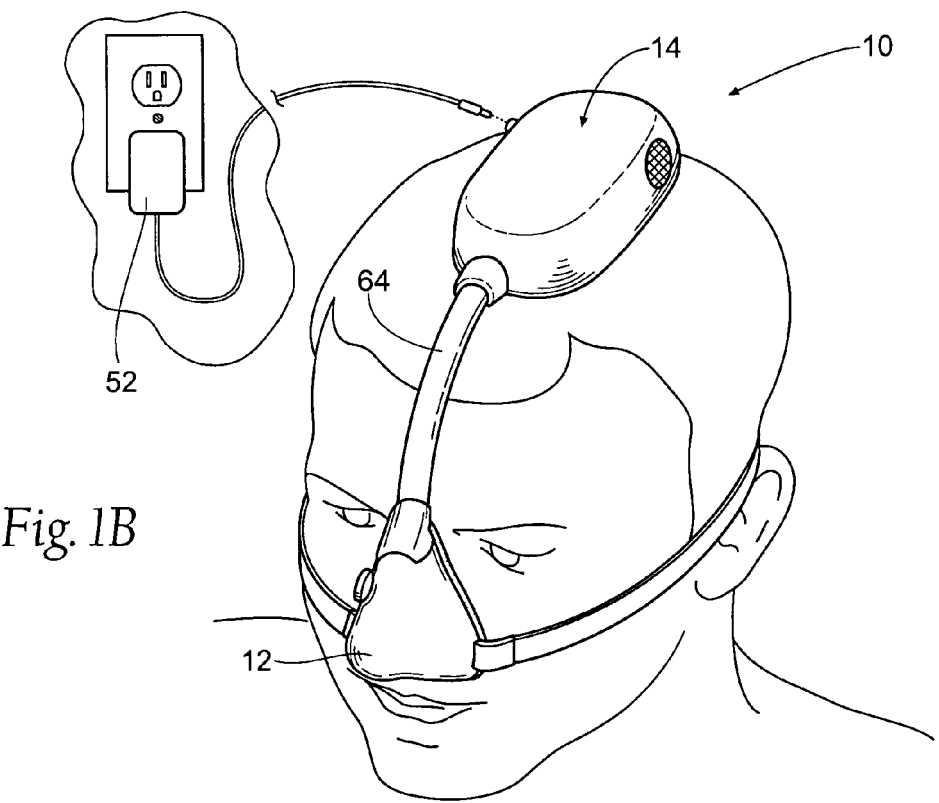
Figure 1C:
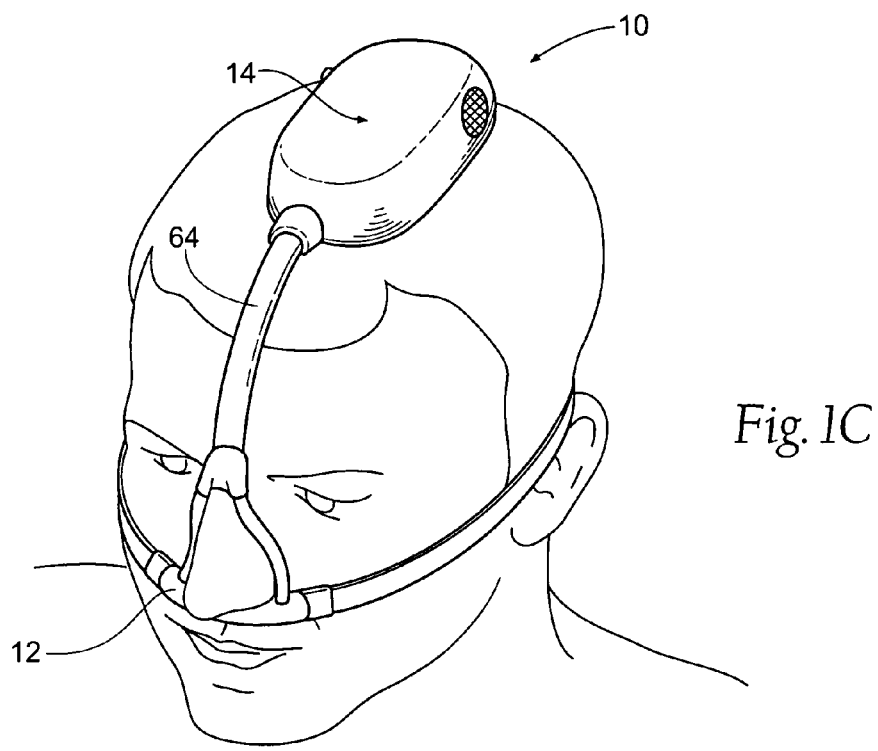

FIGS. 1A to 1D and 2A/B show representative embodiments of a self-contained, intermittent positive airway pressure system 10 for treating sleep apnea, snoring, and other respiratory disorders. The system 10 is sized and configured to be worn by an individual during sleep, in communication with the individual's airway, as, e.g., FIG. 1B and FIG. 2B shows. In use, the system 10 functions to maintain desired positive air pressure conditions in the upper airway during the respiration cycle. The desired positive air pressure conditions are sufficient to resist the collapse of tissue along the airway during sleep, thereby maintaining an open airway that does not block or interfere with airflow to and from the lungs.

The system 10 is "self-contained," meaning that it need not be coupled or "tethered" to an external source of positive air pressure. As will be described in greater detail later, a source of air positive pressure is carried on-board the system 10.

The system 10 is "intermittent," meaning that it supplies positive air pressure to the airway sufficient to resist tissue collapse in the upper airway in a manner that is not continuous. The system 10 supplies positive air pressure to selectively resist collapse of the airway only during a portion of the respiratory cycle. In representative embodiments that will be described in greater detail later, the system 10 supplies positive air pressure sufficient to resist tissue collapse in the upper airway only at desired times before and/or during the inhalation phase of the respiratory cycle. At other times, the system 10 does not supply positive air pressure sufficient to resist tissue collapse in the upper airway. During the exhalation phase, however, the system 10 can also serve to resist the passage of exhaled air, thereby increasing airway pressure during exhalation, just as increased positive pressure is actively provided sufficient to resist tissue collapse in the upper airway before and during at least a portion of the inhalation phase.

The "intermittent" aspect of the system 10 complements the "self-contained" aspect of the system 10. There is a significant energy requirement for actively providing positive pressurized air throughout the respiratory cycle for the duration of a normal sleep cycle, e.g., eight hours. Further, the noise created by a mechanized positive pressure source carried by an individual during sleep should desirably be much less than the noise created by blowers in traditional CPAP consoles, which are both farther from the patient's ears and (being placed within the CPAP console) insulated for sound. The intermittent supply of positive pressure sufficient to resist tissue collapse in the upper airway makes possible, e.g., a reduction in the overall energy requirements of the system 10 and an overall reduction of noise generated during operation of the system 10.

A. The Airflow Director

Figure 1D:
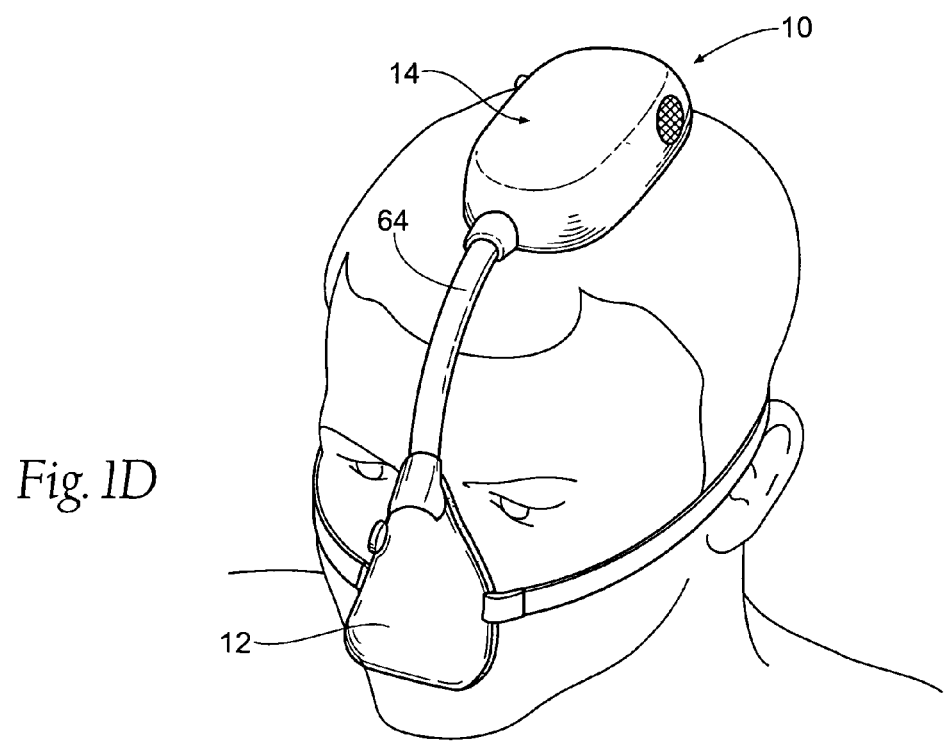

As shown in FIGS. 1A to 1D, the system 10 comprises an airflow director 12 sized and configured to be worn in or over the nose of the individual in communication with an upper airway. The airflow director 12 can comprise a mask that is sized and configured to form an airtight seal over the nose (FIGS. 1A and 1B), or in the nasal nares (FIG. 1C), or over the nose and mouth (FIG. 1D). The mask 12, when properly fitted to an individual, communicates with the upper airway of the individual.

B. The Airflow Regulation Assembly

The system 10 further comprises an airflow regulation assembly 14 communicating with the mask 12. In a first mode, the airflow regulation assembly 14 regulates the supply of air to the mask 12 in synchronization with the native inhalation phase of the respiratory cycle. In a second mode, the airflow regulation assembly 14 regulates the exhaust of air from the mask 12 in synchronization with the native exhalation phase of the respiratory cycle. Intermittently, the airflow regulation assembly 14 increases positive air pressure within the mask 12 and the upper airway sufficient to resist tissue collapse in the upper airway only during a portion of the respiratory cycle. The positive air pressure affirmatively prevents or resists the collapse of tissue in the upper airway that, in the absence of the positive air pressure, could occur to block or otherwise obstruct airflow to and from the lungs.

Figure 2A:
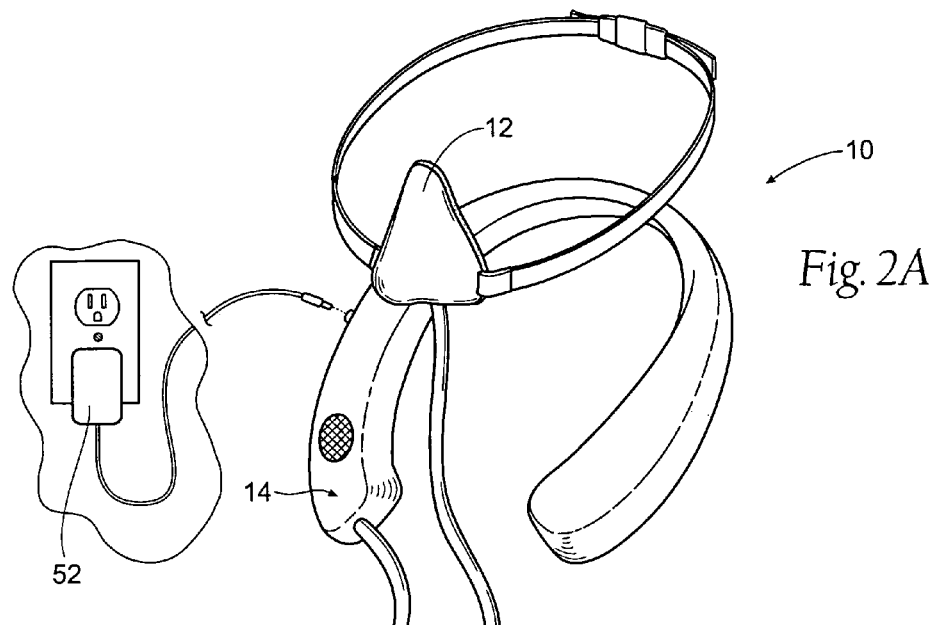
FIGS. 2A and 2B are perspective views of another illustrative embodiment of a self-contained, intermittent positive airway pressure system for treating sleep apnea, snoring, and other respiratory disorders.
Figure 2B:
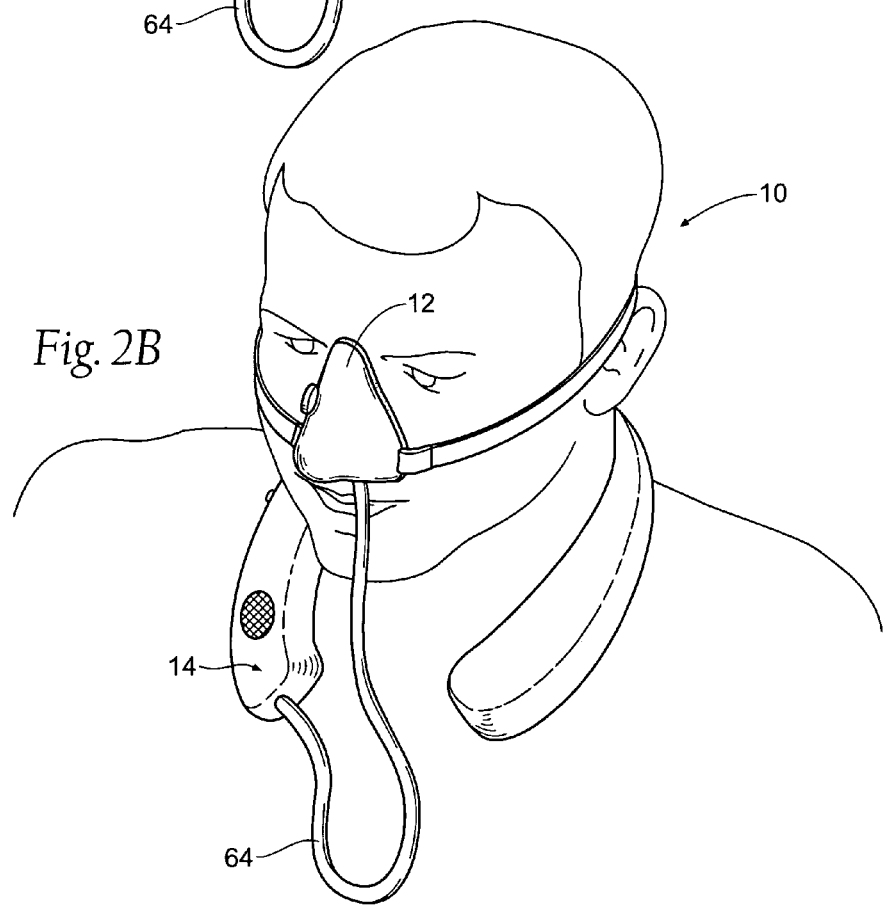

The airflow regulation assembly 14 is desirably sized and configured appropriately for comfortable weight positioning and distribution when worn by an individual. Comfortable weight positioning and distribution can be achieved, e.g., by keeping the weight of the airflow regulation assembly 14 close to the head and on the surfaces of the head that do not typically contact the pillow or bed, one such region being the top of the head (as FIGS. 1A to 1D show), or by placing some or all of the components inside a neck collar that is comfortable and could provide sound dampening (as FIGS. 2A and 2B show). As shown in FIGS. 2A and 2B, the collar can take a form similar to that of a travel neck pillow.

1. The Airflow Manifold

The airflow regulation assembly 14 can be variously constructed. In a representative embodiment, the airflow regulation assembly 14 comprises a housing defining an airflow manifold 16 with one or more airflow channels communicating with the mask 12. The manifold housing is shown in FIGS. 1A to 1D (for wearing on the head) and in FIGS. 2A and 2B (carried within the pillow). The manifold housing is also shown schematically in FIG. 3. The manifold housing can be constructed, e.g., from molded plastic or metal, and be coupled to the mask 12 via flexible tubing 64, as FIGS. 1A to 1D and 2A/B show.

2. The Mask Inlet and Outlet Valves

Figure 3:
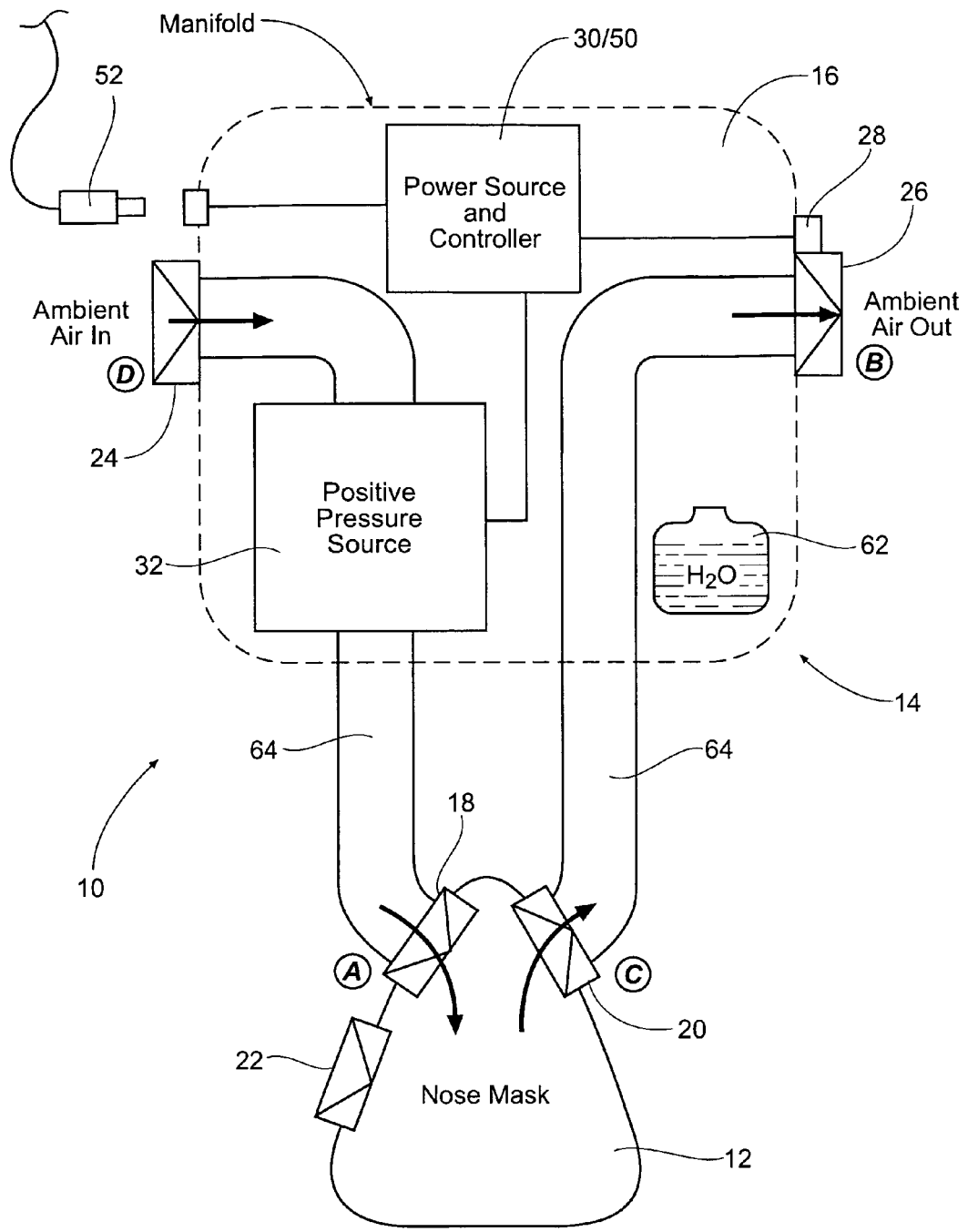
FIG. 3 is a general schematic view of a self-contained, intermittent positive airway pressure system shown in FIGS. 1A to 1D or FIGS. 2A and 2B.

As shown schematically in FIG. 3, the airflow regulation assembly 14 further includes at least one mask inlet valve 18 (designated A in the Figures) that communicates with the airflow manifold 16. The mask inlet valve 18 serves to regulate the inflow of air into the mask 12 through the airflow manifold 16 during an inhalation phase of the respiratory cycle. The mask inlet valve 18 is sized and configured for one-way flow operation, allowing air flow into the mask 12, but blocking air flow out of the mask 12. The mask inlet valve 18 comprises a one-way valve that allows air to flow in when pressure in the mask 12 is less than pressure outside the mask 12, but which closes when internal pressure exceeds external pressure.

The airflow regulation assembly 14 also includes at least one mask outlet valve 20 (designated C in the Figures). The mask outlet valve 20 serves to regulate the outflow of air from the mask 12 through the airflow manifold 16 during an exhalation phase of the respiratory cycle. The mask outlet valve 20 is sized and configured for one-way flow operation, allowing air flow out of the mask 12, but blocking air flow into the mask 12. The mask outlet valve 20 comprises a one-way valve that allows air to flow out when pressure in the mask 12 is greater than pressure outside the mask 12, but which closes when internal pressure is less than external pressure.

The mask inlet valve 18 and the mask outlet valve 20 can each comprise, e.g., a one way mechanical check valve, such as a ball check valve, a swing check valve, a butterfly check valve, a clapper valve, a duckbill valve, a dual check valve, or a lift check valve. The valve can also be a diaphragm valve or any other equivalent self-closing, one-way valve. Alternatively, or in combination, the mask inlet valve 18 and the mask outlet valve 20 can each comprise a low-power electrically or pneumatically actuated valve.

In the case of a nose mask 12 (e.g., as FIGS. 1A, 1B, 1D, 2A, and 2B show), the nose mask 12 includes an additional one-way valve 22 directly between the nose mask 12 and the ambient air (i.e. not through the manifold 16). This additional one-way valve 22 opens to allow ambient air inflow whenever the pressure in the mask 12 falls below ambient air pressure. If pressure in the mask 12 exceeds ambient air pressure (e.g. during exhalation or during inhalation when the airflow regulation assembly 14 increases positive air pressure within the mask 12 and the upper airway during a portion of the respiratory cycle) the additional one-way valve 22 closes. The additional one-way valve 22 can comprise, e.g., a one way mechanical check valve, a diaphragm valve, or any other equivalent self-closing, one-way valve.

3. The Ambient Air Inlet and Outlet Valve

In a representative embodiment, the airflow regulation assembly 14 further comprises at least one ambient air inlet valve 24 (designated D in the Figures) that communicates with the airflow manifold 16. The ambient air inlet valve 24 serves to regulate the inflow of fresh ambient air through the manifold 16 into the mask 12 (and thus into the upper airway) in concert with the mask inlet valve 18 during an inhalation phase of the respiratory cycle. The ambient air inlet valve 24 is sized and configured for one-way flow operation, allowing air flow in from the ambient atmosphere into the mask 12, but blocking air flow from the mask 12 out to the ambient atmosphere. The ambient air inlet valve 24 can comprise a one-way valve that allows air to flow in when pressure in the manifold 16 is less than pressure outside the manifold 16, but which closes when internal pressure exceeds external pressure.

The airflow regulation assembly 14 also includes at least one ambient air outlet valve 26 (designed B in the Figures) that communicates with the airflow manifold 16. The ambient air outlet valve 26 serves to regulate the outflow of spent air through the airflow manifold 16 from the mask 12 (i.e., from the upper airway) to the ambient atmosphere in concert with the mask outlet valve 20 during an exhalation phase of the respiratory cycle. The ambient air outlet valve 26 is sized and configured for one-way flow operation, allowing air flow in out to the ambient atmosphere, but blocking air flow in from the ambient atmosphere. The ambient air outlet valve 26 can comprise a one-way valve that allows air to flow out when pressure in the manifold 16 is greater than pressure outside the manifold 16, but which closes when internal pressure is less than external pressure.

Like the mask inlet and outlet valves 18 and 20, the ambient air inlet valve 24 and the ambient air outlet valve 26 can each comprise, e.g., a one way mechanical check valve, such as a ball check valve, a swing check valve, a butterfly check valve, a clapper valve, a duckbill valve, a dual check valve, or a lift check valve. Like the mask inlet and outlet valves, the ambient air inlet and outlet valve can also comprise a diaphragm valve or any other equivalent self-closing, one-way valve. Alternatively, or in combination, the ambient air inlet valve 24 and the ambient air outlet valve 26 can each comprise a low-power electrically or pneumatically actuated valve. For example, the ambient air outlet valve 26 can, alternatively, comprise an electro-mechanically activated valve, actuated, e.g., by an electrical solenoid 28, as shown in FIG. 3. In this arrangement, the ambient air outlet valve 26 is electrically closed by an airflow regulation controller 30 when the airflow regulation assembly 14 increases positive air pressure within the mask 12 and the upper airway during a portion of the respiratory cycle, as will be described in greater detail later.

4. The Source of Positive Pressure

The airflow regulation assembly 14 further comprises a source of positive pressure 32 communicating with the airflow manifold 16. In the representative embodiment, the source of positive pressure 32 is physically carried within the manifold 16. The mask inlet valve 18 (designated A) and the ambient air inlet valve 24 (designated D) communicate with the source of positive pressure 32. The source of positive pressure 32 can be selectively activated to supply positive pressure in an intermittent manner during a portion of the respiratory cycle to augment the pressure of ambient air in the upper airway sufficient to resist tissue collapse in the upper airway.

Figure 8A:
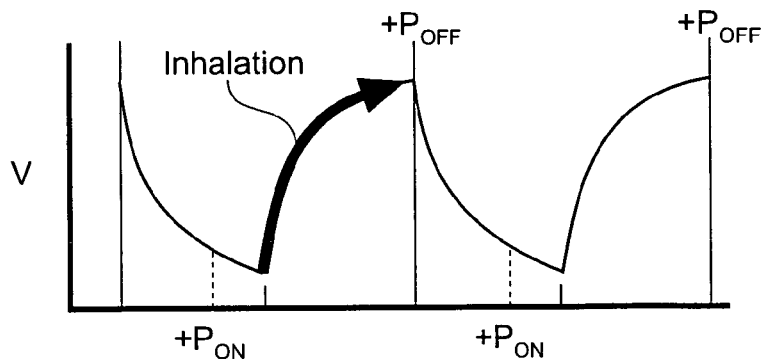
FIGS. 8A and 8B are schematic views a self-contained, intermittent positive airway pressure system as shown in FIGS. 1A to 1D or FIGS. 2A and 2B, which includes a positive pressure source comprising a pre-charged air reservoir, FIG. 8A showing the system during inhalation and FIG. 8B showing the system during exhalation.
Figure 8A:
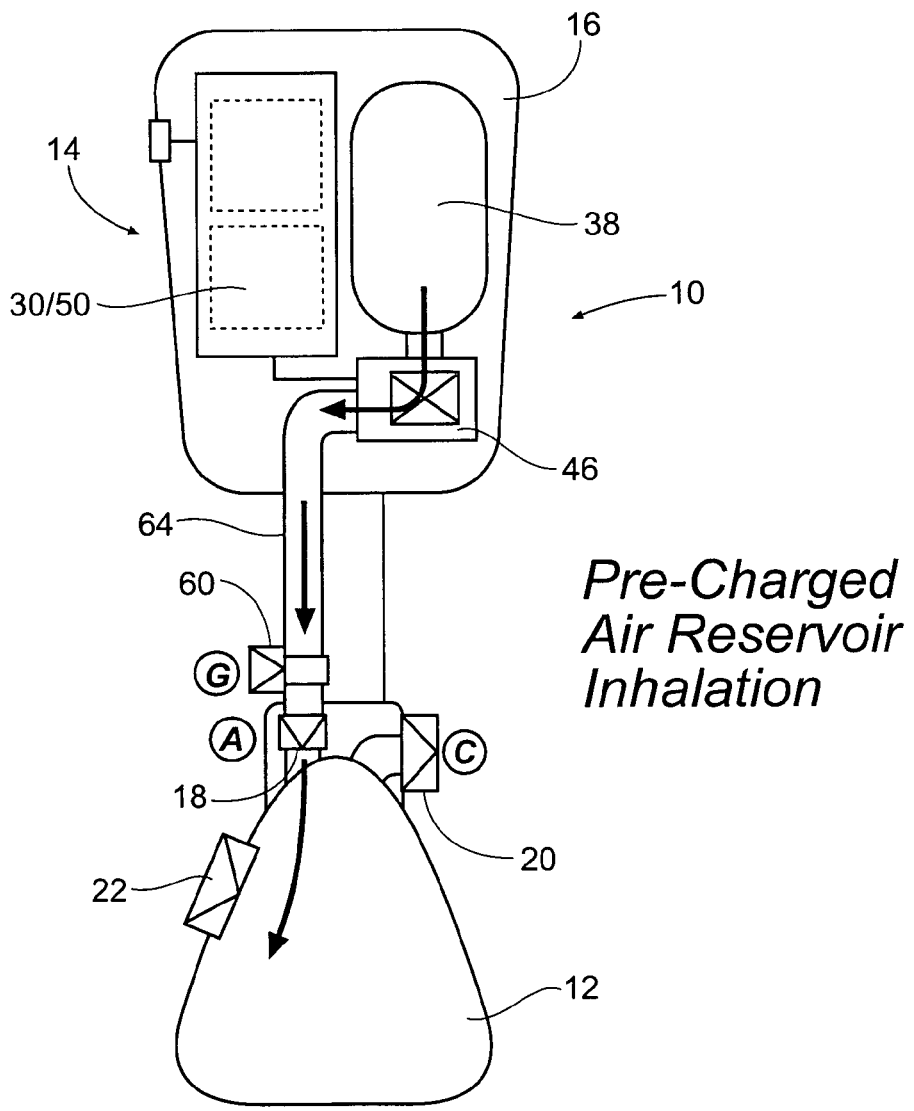
Figure 8B:
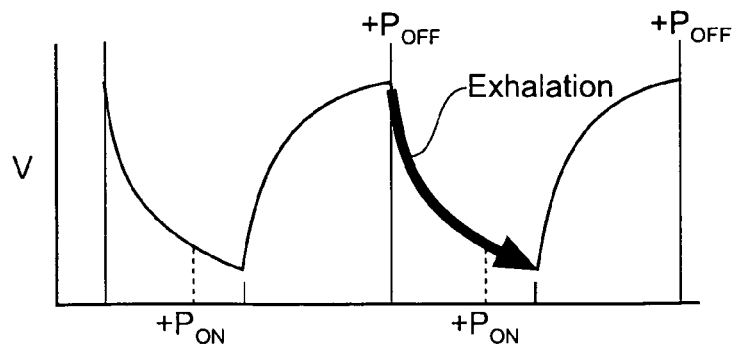
Figure 8B:
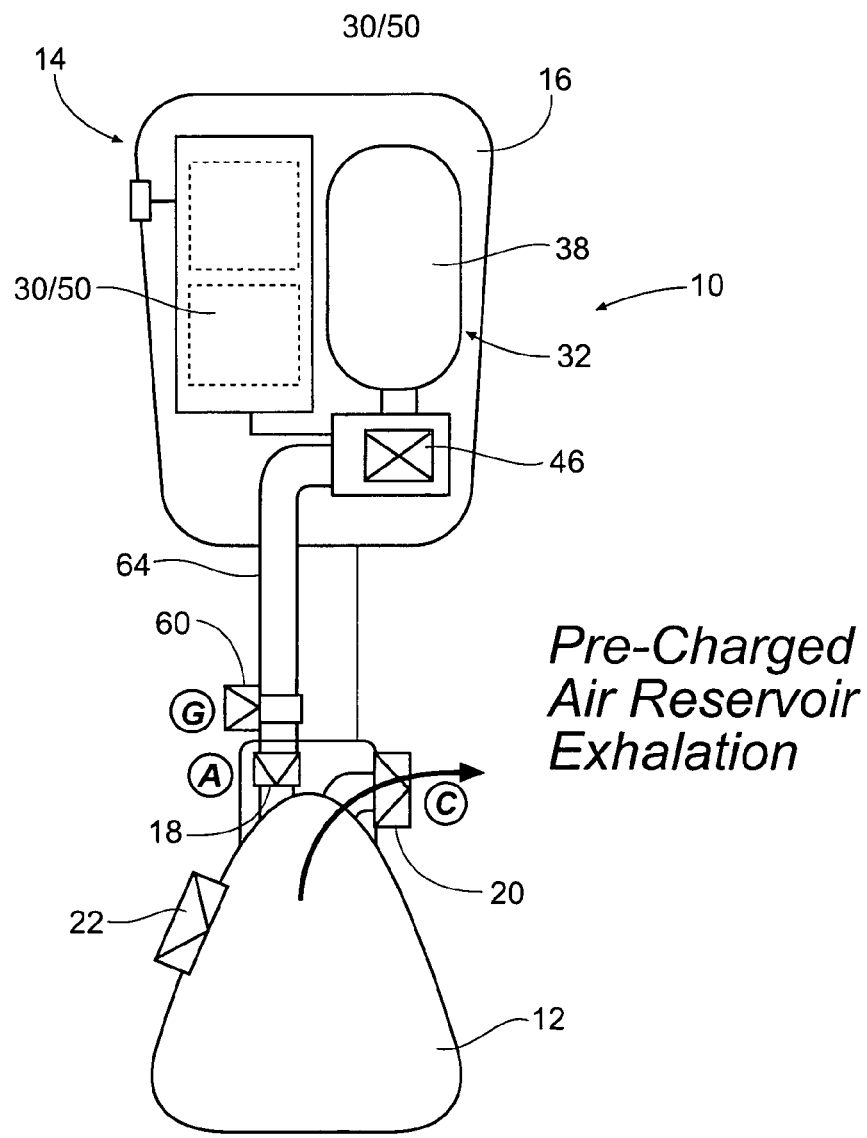
Figure 9A:
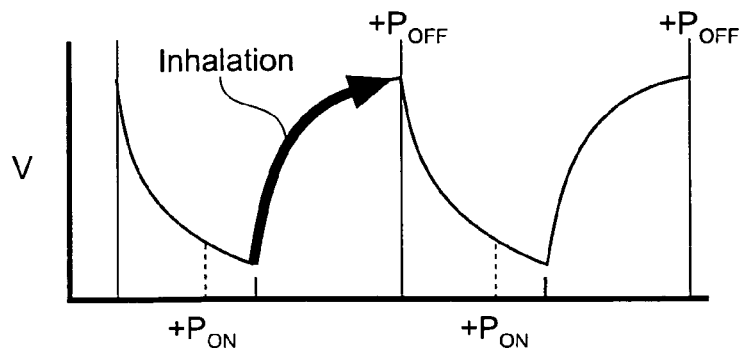
FIGS. 9A and 9B are schematic views a self-contained, intermittent positive airway pressure system as shown in FIGS. 1A to 1D or FIGS. 2A and 2B, which includes a positive pressure source comprising an air reservoir charged by a blower, FIG. 9A showing the system during inhalation and FIG. 9B showing the system during exhalation.
Figure 9A:
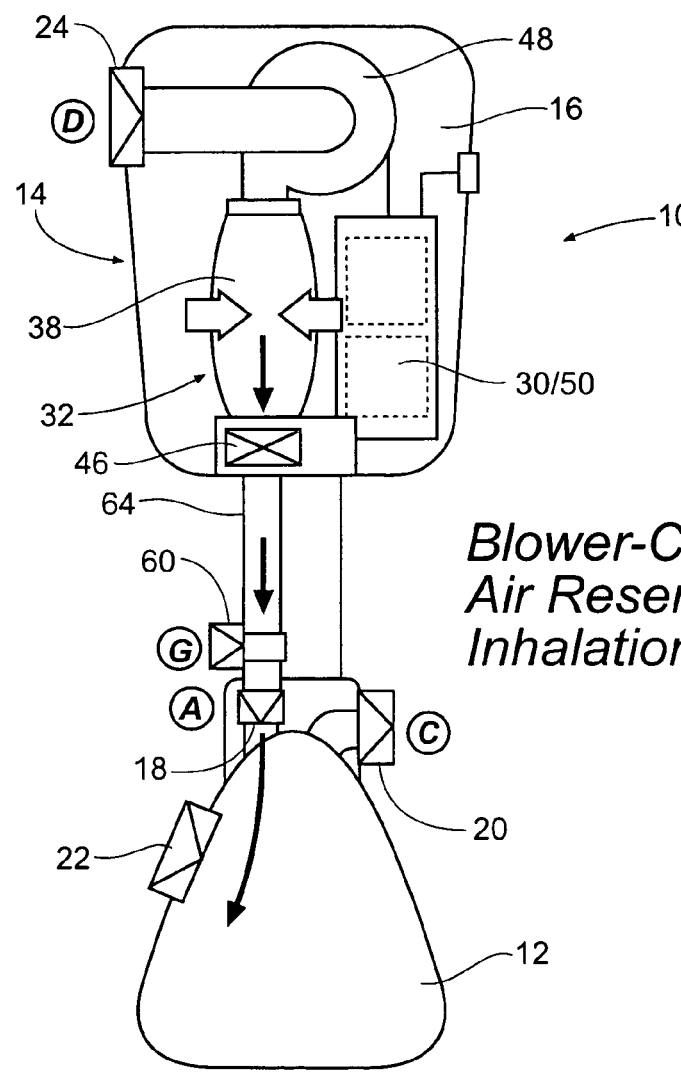
Figure 9B:
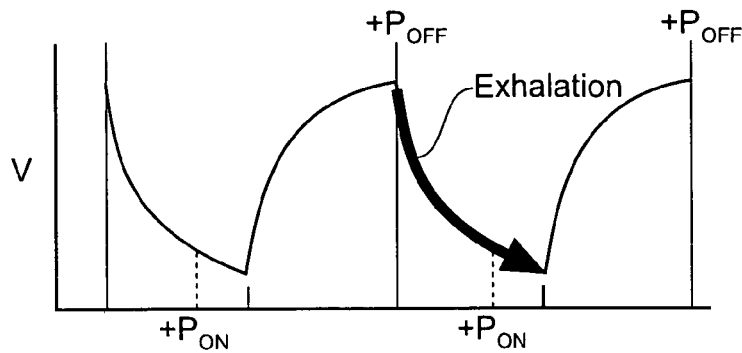
Figure 9B:
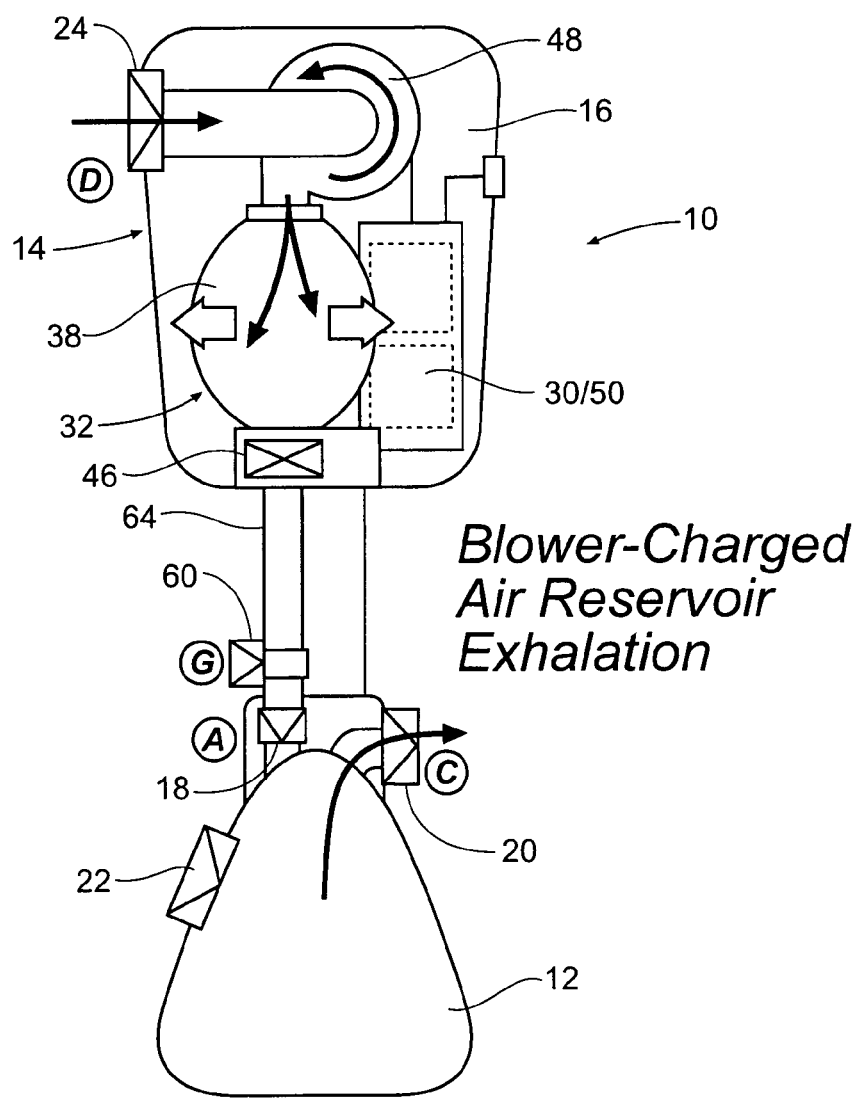

The source of positive pressure 32 can comprise, e.g., a powered turbine 34 (see FIGS. 4A/B), or a powered blower 36 (see FIGS. 6A/B), or an air pressure reservoir or bladder 38 (see FIGS. 8A/B), or combinations thereof (see FIGS. 9A/B).

a. Powered Turbine

Figure 4A:
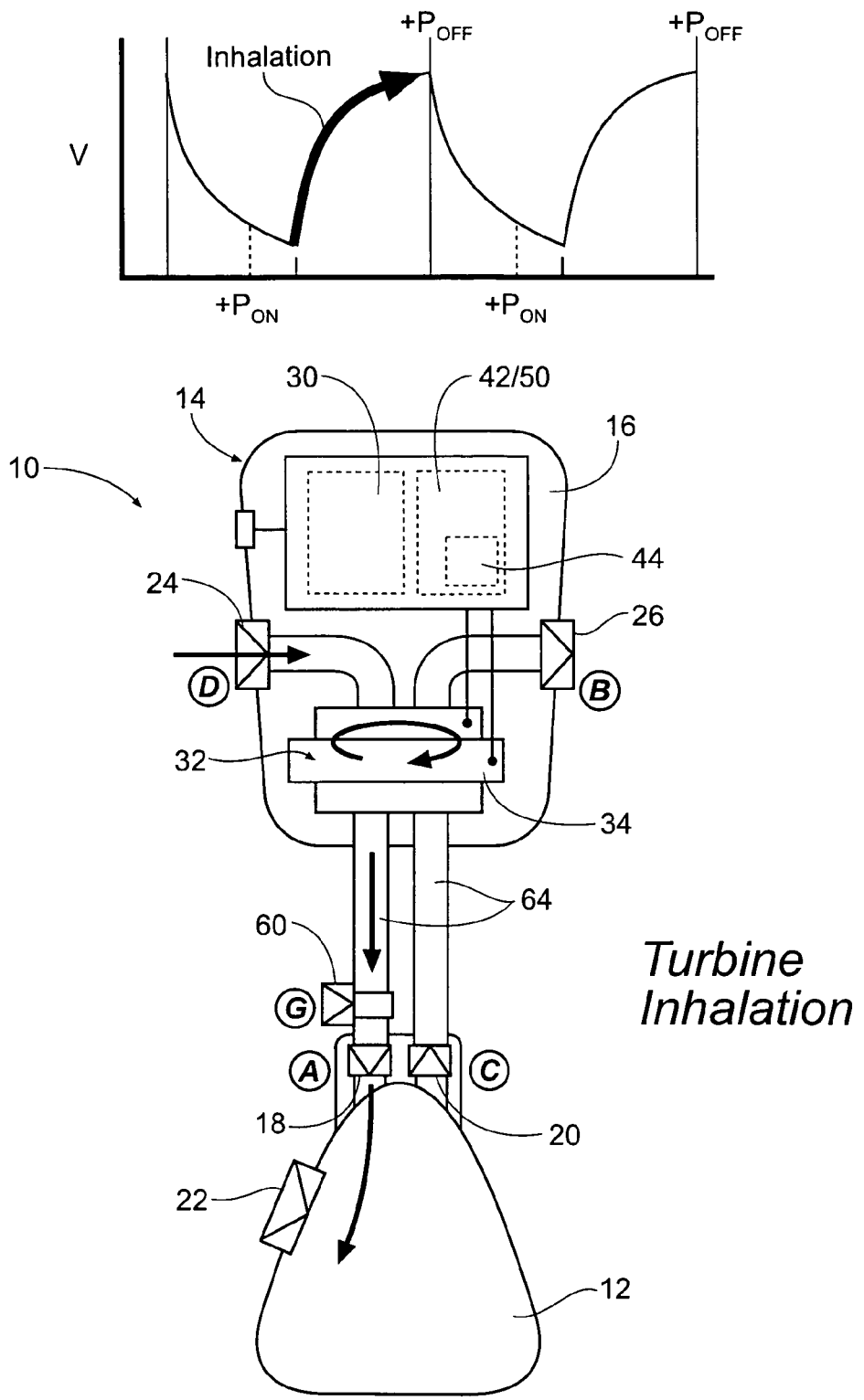

As FIG. 4A shows, a powered turbine 34 in the manifold 16 communicating with the mask inlet valve 18 and ambient air inlet valve 24 can serve to intermittently supply positive air pressure before and/or during an inhalation phase to increase the air pressure in the upper airway sufficient to resist tissue collapse in the upper airway, thereby preventing or resisting tissue collapse.

As FIGS. 4B also show, a turbine 34 in the manifold in communication with the mask outlet valve 20 (designated C) also provides the added capability of rotating in response to the passage of air during the act of exhaling, and thereby mechanically resisting the passage of air during exhalation. The resistance of the turbine 34 increases air pressure in the upper airway during exhalation, in the same way pursing one's lips increases upper airway pressure during exhalation.

When coupled to a generator 40 (see FIG. 4B and FIG. 5), the spinning turbine 34 can also serve to generate energy for storage and later use by the turbine 34 (see FIG. 4A) (or by a separate blower 36) to generate positive air pressure for application during an inhalation phase.

More particularly, power can be created by a turbine 34 during an exhalation phase and stored in a battery, capacitor, or similar storage element 42 (shown in FIGS. 4A/B).

Power generated by a turbine 34 can be expressed by the equation: $P=0.5\rho Av^3$ where:

P is Power.

$\rho$ (rho) is the density of the air.

A is the area of the turbine 34.

v is the velocity of the air.

Additionally, when calculating for a generator: $P=0.5\rho Av^3 CpNgNb$ where:

Cp is the coefficient of power.

Ng is the generator efficiency.

Nb is the bearing/gear efficiency.

The source of positive pressure 32 can incorporate several possible turbine designs. For example, the source of positive pressure 32 can include a turbine 34 that always spins the same direction to maintain momentum (see FIG. 4A). As another example, the source of positive pressure 32 can include a turbine 34 that reverses direction upon inhalation (FIG. 4A) and exhalation (FIG. 4B). As another example, the source of positive pressure 32 can include a series or array of multiple smaller turbines 34 which act in the aggregate. Turbine blade design encompasses many shapes to provide optimal aerodynamics. These shapes are known to those of ordinary skill in the art.

b. Powered Blower

Figure 6A:
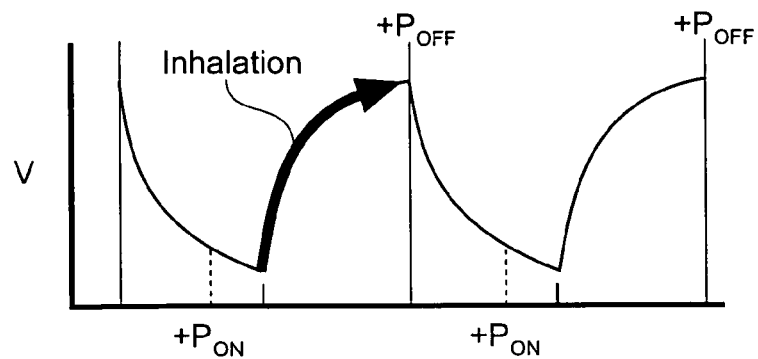
FIGS. 6A and 6B are schematic views a self-contained, intermittent positive airway pressure system as shown in FIGS. 1A to 1D or FIGS. 2A and 2B, which includes a positive pressure source comprising a blower, FIG. 6A showing the system during inhalation and FIG. 6B showing the system during exhalation.
Figure 6A:
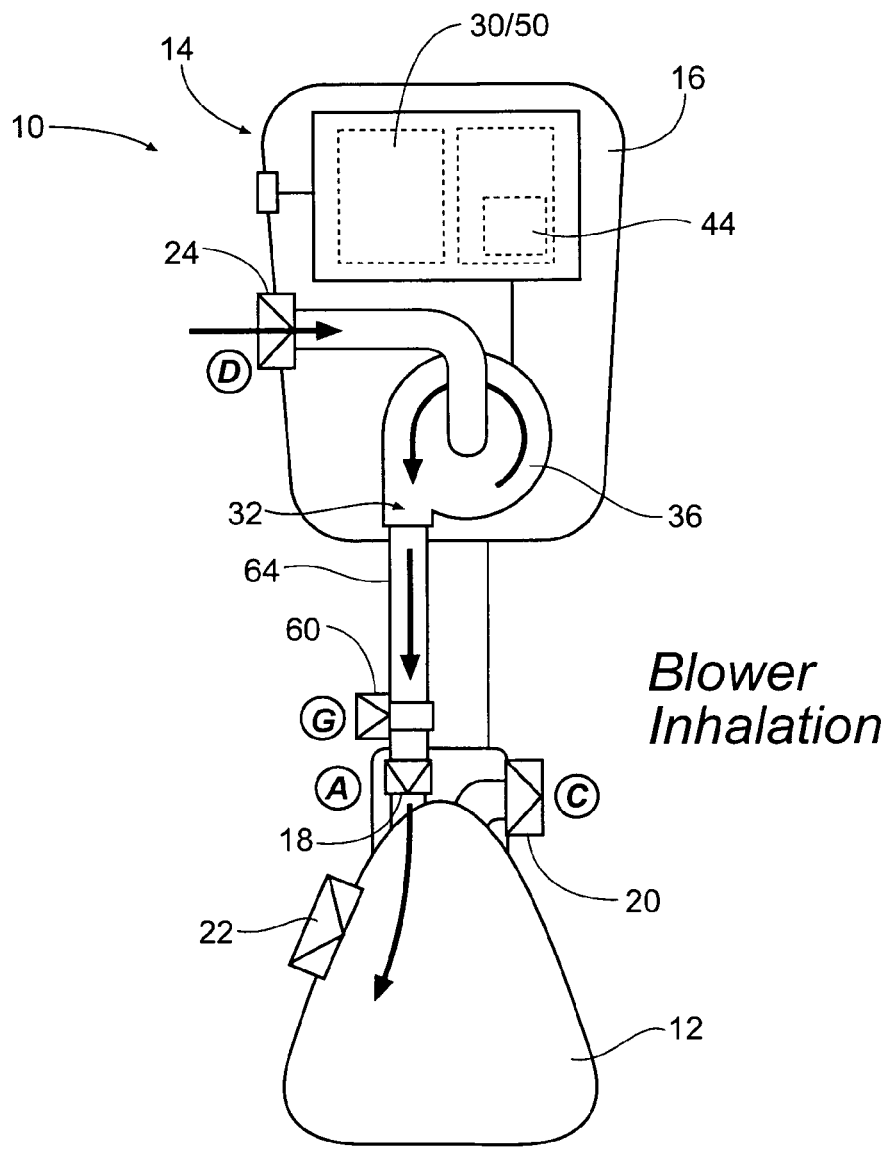
Figure 6B:
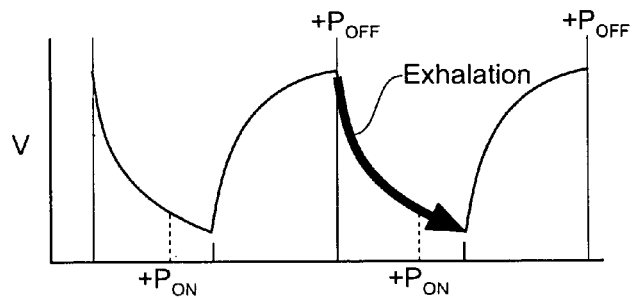
Figure 6B:
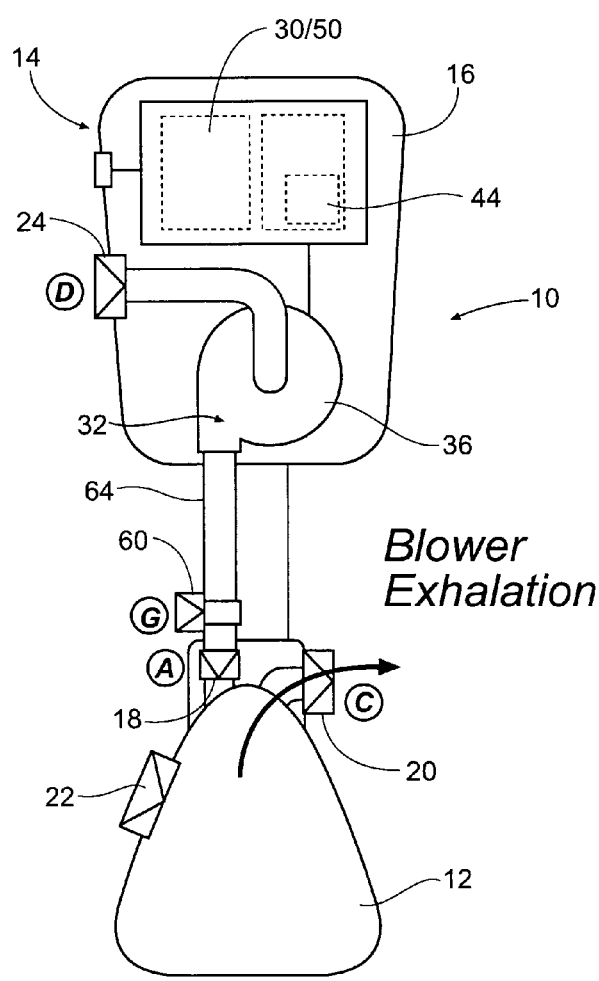

As shown in FIGS. 6A/B, as another example, the source of positive pressure 32 can include a powered blower 36 in the manifold 16 communicating with the mask inlet valve 18 (designated A) and ambient air inlet valve (designated D). As used in this application, a "blower" differs from a "turbine" in that a blower 36 will not rotate in response to the passage of exhaled air. A blower 36 requires power to rotate.

In one embodiment, the blower 36 can run continuously at a low or idle power, drawing in ambient air and conveying it into the mask 12 via the mask inlet valve 18. At idle power, the blower 36 does not increase pressure sufficient to resist tissue collapse in the upper airway. At the desired time, the power to the blower 36 is increased to increase the rotational speed of the blower 36 to generate the requisite magnitude of positive air pressure for delivery into the airway sufficient to resist tissue collapse in the upper airway. This mode of operation allows the blower 36 to consume less power (and make less noise). Alternatively, no power can be supplied to the blower 36 until the desired time, at which time full power is supplied to the blower 36 to generate pressurized air for conveyance into the airway sufficient to resist tissue collapse in the upper airway.

Figure 7A:
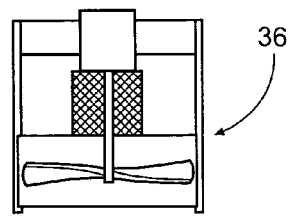
FIGS. 7A to 7C are perspective views of illustrative embodiments of a blower that can be used in the system shown in FIGS. 6A and 6B.
Figure 7B:
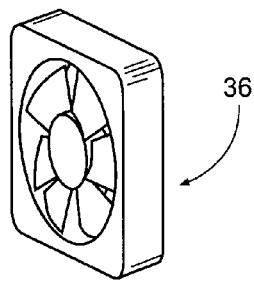
Figure 7C:
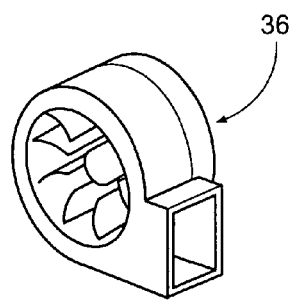

Representative mechanical configurations for a blower 36 are shown in FIGS. 7A, 7B, and 7C. The blower 36 can include multiple heads, allowing it to compress and deliver more air at a lower speed, thereby producing less noise.

A powered blower 36/turbine 34 can include a noise cancellation device 44 (see FIG. 6A) to create noise cancellation waves at specific wavelengths to offset the noise created by the blower 36/turbine 34. In this arrangement, the blower 36/turbine 34 and the noise cancellation device 44 are synchronized such that the noise cancellation device 44 provides canceling waves specific to the wavelength of the noise created by the blower 36/turbine 34 at a given speed. As the blower 36/turbine 34 increased or decreased speed, the noise cancellation device 44 would provide different frequency outputs. By synchronizing the two, the noise canceling function would not have to first "hear" the noise before it determined the optimal wavelength output to offset the noise.

c. Air Reservoirs

As shown in FIGS. 8A/B, as another example, the source of positive pressure 32 can include one or more air pressure reservoirs 38 in the manifold 16 communicating with mask inlet valve 18. In this arrangement, the airflow regulation assembly 14 includes at least one electrically actuated valve 46 that opens to release the stored air pressure to the mask 12 (and upper airway) sufficient to resist tissue collapse in the upper airway at the desired time.

In the embodiment shown in FIGS. 8A/B, the air pressure reservoir(s) 38 are charged outside of the airflow regulation assembly 14 prior to sleep and inserted into the airflow regulation assembly 14 at the beginning of the sleep cycle.

In another embodiment shown in FIGS. 9A/B, the airflow regulation assembly 14 includes an air charging blower 48 in the manifold 16 that communicates with the air pressure reservoirs 38. The air charging blower 48 is operated at a low speed (e.g., by an on-board battery) sufficient to maintain the air reservoir(s) in a charged condition for use. A series of reservoirs 38, as few as two but as many as ten or more could be used, with one reservoir 38 being used to supply the positive pressure during a portion of the respiratory cycle, and the others 38 being simultaneously recharged by the charge blower 48 continuously for use during the next respiratory cycle.

d. Energy Sources

As FIG. 3 generally shows, the source of energy 50 for an intermittently powered turbine 34 or intermittently powered blower 36, and/or the electrically actuated valves can be provided by, e.g., a rechargeable battery or capacitor that is periodically charged prior to use by a power cord or battery charging unit 52 coupled to an AC power source (also shown for purposes of illustration in FIGS. 1A and 2A); or a disposable battery or batteries that are periodically replaced. Regardless, the batteries or capacitor are sized and configured to be carried on-board the airflow regulation assembly 14, as FIG. 3 generally shows.

Alternatively, or in combination, some or all of the energy required to operate an intermittently powered turbine 34 or intermittently powered blower 36, and/or electrically actuated valves can be provided by an energy source 42 that is replenished or charged by a charging element carried on-board the airflow regulation assembly 14 by the energy created by the native act of exhalation. For example, as shown in FIGS. 4B and 5, and as previously described, a turbine 34 coupled to a generator 40 carried by the airflow regulation assembly 14 can generate electrical energy in response to passage of air during exhalation. This energy is transferred to a battery, capacitor, or equivalent energy storage element 42 carried on-board the airflow regulation assembly 14 (shown in FIG. 4B), to subsequently power the turbine 34 or an intermittently powered blower 36, and/or electrically actuated valves when the supply of positive air pressure is required.

The above-described embodiments make possible a cordless, fully wearable, self-contained system 10 (as FIGS. 1A/B and 2A/B show), one in which, during the sleep cycle, the individual is not tethered to anything external of the body. In an alternative embodiment, the energy source carried on-board the airflow regulation assembly 14 can include a small, flexible lightweight AC cord that magnetically connects to the airflow regulation assembly 14, charging the power sources and providing power for use at the beginning of the sleep cycle. Upon charging, the magnetic connect disconnects for fully tetherless use for the remainder of the sleeping cycle. The minimal power cord allows for a smaller battery and weight.

5. Exhalation Resistance

As FIGS. 4B, 10A/B, and 11 show, the airflow regulation assembly 14 can also comprise various means 54 for restricting airflow during exhalation from within the mask 12 to outside of the mask 12.

The means 54 for restricting airflow during exhalation can comprise, e.g., one or more exhaust holes 56 communicating with the ambient air outlet valve 26 with limited cross-sectional area (see FIGS. 10A/B). The exhalation resistance exhaust holes 56 desirably include adjustable cross-sectional areas (e.g., in the form of rotational port arrays shown in FIGS. 10A/B), so that a user or healthcare professional can adjust these.

Alternatively, or in combination, as described above, the means 54 for restricting airflow can comprise one or more turbines 34 (see FIGS. 4B) or other means in the manifold 16 communicating with the ambient air outlet valve 26 (designated B) that create airflow resistance within the manifold 16. Reliance on resistance created by the means 54 during forced exhalation to create increased pressure in the upper airway during some or all of expiration makes possible the use of a source of positive pressure 32 that does not have to be on continuously. The source of positive pressure 32 need only be operated to provide positive pressure sufficient to resist tissue collapse in the upper airway during a portion of the respiratory cycle.

As also described above, a turbine 34 (see FIG. 4B) can itself also serve to generate for storage energy in the form of mechanical, chemical or electrical energy. At the completion of exhalation (or at some point before or after the completion of exhalation), the turbine 34 or a blower 36 can use the stored energy (with or without other stored energy in the device, such as a battery) to blow fresh air into the mask 12 (as shown in FIG. 4A) sufficient to resist tissue collapse in the upper airway. This may occur throughout inhalation, or during a portion of inhalation, or prior to the start of inhalation. In this way, the airflow regulation assembly 14 provides both increased airway pressure during exhalation as well as increased pressure before or during at least a portion of inhalation sufficient to resist tissue collapse in the upper airway.

Figure 14A:
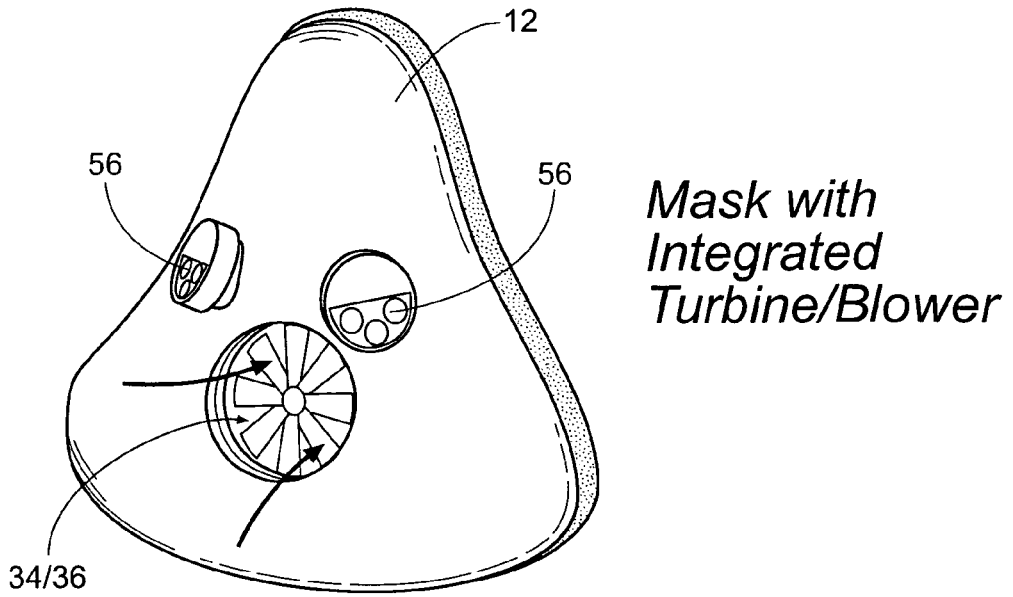
FIGS. 14A and 14B are perspective views showing representative embodiments of a mask that can be incorporated into a self-contained, intermittent positive airway pressure system as shown in FIGS. 1A to 1D or FIGS. 2A and 2B, the mask having an integrated source of positive pressure comprising a turbine 34 or blower 36, as well as exhalation resistance ports.
Figure 14B:
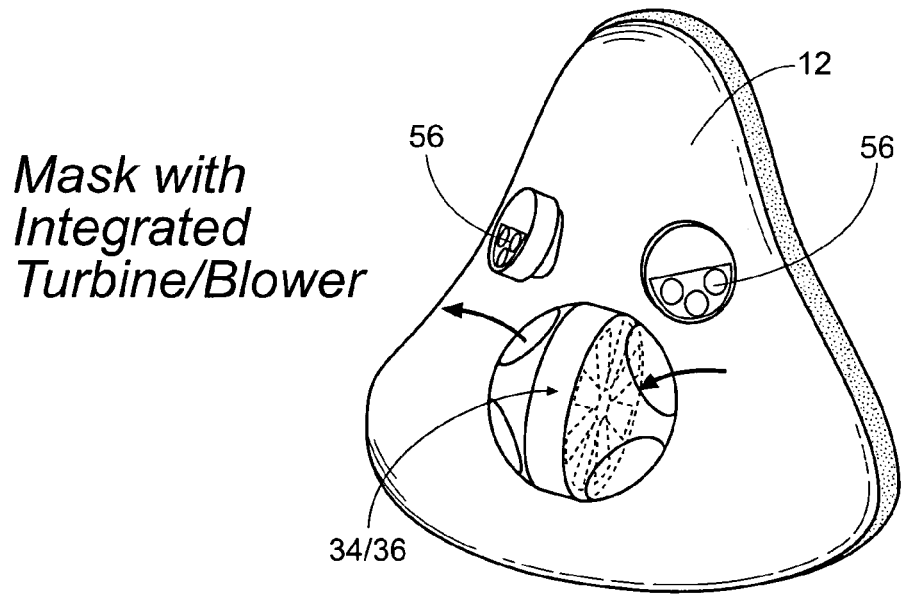

As FIGS. 14A and 14B show, the mask 12 can carry an integrated turbine 34 or blower 36, with communication vents for inhalation and exhalation. Such a mask 12 could be made to fit over the nose and mouth, or just the nose of the user. The flow channels and valves of the airflow regulation assembly 14 shown schematically in FIGS. 4A/B (turbine 34) or FIGS. 6A/B (blower 36) may likewise be fully or partially integrated into the mask 12, to function during inhalation and exhalation in the manner previously described. For example, upon inhalation by the user, mask inlet valve 18 (A) is opened by the low pressure created by the user. Subsequently, ambient air outlet valve 26 B and mask outlet valve 20 (C) are pulled closed by the lower pressure. Ambient air inlet valve 24 (D) opens from the lower pressure to allow fresh air in from the atmosphere. At a predetermined or calculated time (calculated by detection of change in pressure, turbine speed, or valve position), the power assisted turbine 34/blower 36 sequence is initiated to provide additional pressure before and/or during inhalation, sufficient to resist tissue collapse in the upper airway. Upon initiation of exhalation by the user, mask outlet valve 20 (C) is opened by the high pressure created by the user. Mask inlet valve 18 (A) and ambient air inlet valve 24 (D) are closed by the higher pressure. Air exits the user's mask 12 through the mask outlet valve 20 (C). When a turbine 34 is present (as in FIGS. 4A/B), the mask outlet valve 20 (C) can direct the exhaled air into the turbine 34. The turbine 34 provides resistance to the user's exhalation. Resistance exhaust ports 56 can also be present in the mask 12, as shown in FIGS. 14A/B, to augment the resistance of the turbine 34. The exhalation resistance aids in keeping the user's airway open during expiration due to the increased air pressure. Expired air escapes to atmosphere after passing through the turbine 34/blower 36 through ambient air outlet valve 26 (B). During this phase the turbine 34 may also be used to collect and store energy provided by the user. The turbine 34 may rotate in one direction during inhalation and in an opposite direction during exhalation (as shown by opposite rotational arrows FIG. 4A to FIG. 4B).

In another embodiment (see FIG. 11), the means 54 for restricting airflow can comprise, by itself or in combination with exhaust holes 56 with limited area, a flap 58 around the outer edge of the mask 12. The flap 58 is sized and configured to lift off the user's face and create an opening between the mask 12 and skin through which air can escape in a controlled manner. Upon inhalation, the flap 58 is held tight to the face, to not provide a channel for air exchange. Upon exhalation, the flap 58 opens. An additional benefit to this design is the cycling on and off of the contact between the mask 12 and the user's skin. This reduces the amount of irritation and sores created by the mask 12 on the face.

6. Representative Operation

Figure 12:
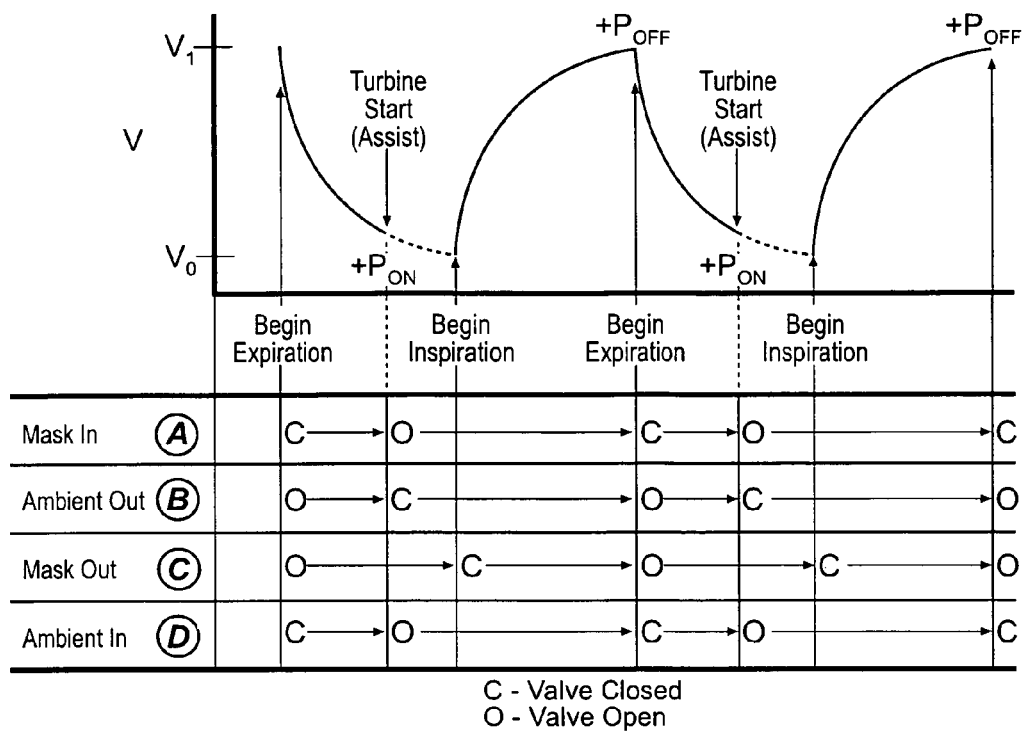
FIG. 12 is a schematic view of a self-contained, intermittent positive airway pressure system as shown in FIGS. 1A to 1D or FIGS. 2A and 2B, showing the operation of the airflow regulation assembly that the system incorporates during the inhalation and exhalation phases of a respiratory cycle.
Figure 12:
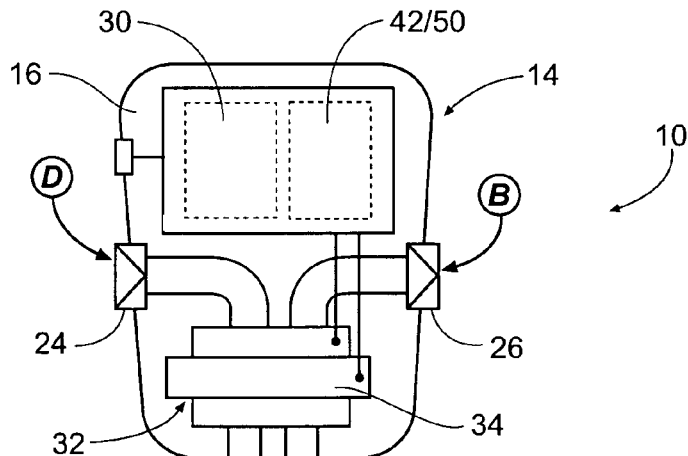
Figure 12:
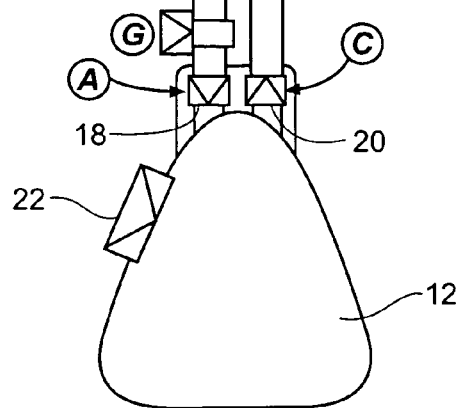

FIG. 12 shows the coordinated operation of the manifold 16, the pressure source 32, and the valve components (A to D) of a representative airflow regulation assembly 14 during inhalation and expiration phases of the respiratory cycle. In FIG. 12, the mask inlet valve 18 (A), the mask outlet valve 20 (C), the ambient air inlet valve 24 (D), and the ambient air outlet valve 26 (B) each comprises a mechanical one way check valve that opens and closes in predetermined one-way flow directions, as above described, in response to pressure differentials across the respective valve.

During a typical inhalation phase (i.e., during the first mode of operation), the pressure differential generated across the mask inlet valve 18 in the mask 12 by the act of inhalation will open the mask inlet valve 18 (A). The pressure differential generated across the ambient air inlet valve 24 by the act of inhalation will also open ambient air inlet valve (D). Conversely, the same pressure differentials will close the mask outlet valve 20 (C) and the ambient air outlet valve 26 (B). Ambient air is supplied via the opened ambient air inlet valve 24 (D) and mask inlet valve 18 (A) into the mask 12 and, from there, into the upper airway.

During a typical exhalation phase (i.e., during the second mode of operation), the pressure differential generated across the mask outlet in the mask 12 by the act of exhalation will open the mask outlet valve 20 (C). The pressure differential generated across the ambient air outlet valve 26 by the act of exhalation will also open ambient air outlet valve 26 (B). Conversely, the same pressure differentials will close the mask inlet valve 18 (A) and the ambient air inlet valve 24 (D). Spent air is exhausted from the upper airway via the opened ambient air outlet valve 26 (B) and mask outlet valve 20 (C) from the mask 12 and, from there, into the ambient atmosphere.

The source of positive pressure 32 can be intermittently operated to augment the pressure of ambient air in the upper airway sufficient to resist tissue collapse in the upper airway. For example, at a desired time during an inhalation phase, the source of positive pressure 32 can be activated to increase the pressure of ambient air in the upper airway sufficient to resist tissue collapse in the upper airway. The source of positive pressure 32 is deactivated during the next successive exhalation cycle. As a result, collapse of tissue structures within the upper airway are prevented or resisted during all or a portion of the inhalation phase. As another example, at a desired time prior to the initiation of inhalation (e.g., near the end of a preceding exhalation phase), the source of positive pressure 32 can be activated to increase the pressure of ambient air in the upper airway sufficient to resist tissue collapse in the upper airway. The source of positive pressure 32 is deactivated at the beginning of the next successive exhalation cycle. As a result, collapse of tissue structures within the upper airway are prevented or resisted before as well as during the inhalation phase.

In FIGS. 4A/B, 6A/B, 8A/B, and 9A/B, the airflow regulation assembly 14 further includes, instead of the one-way valve 22, or in combination with the one-way valve 22, a vent valve 60 (designated G) that can be opened to provide the user with direct access to fresh ambient air in a path that bypasses the source of positive pressure 32. For example, the vent valve 60 could serve as a safety valve, to ensure the user can inhale in the event that the source of positive pressure 32 malfunctions. The vent valve could be independently controlled, or controlled by a sensor or other electronic controls, or could be pressure controlled, i.e. always open when the pressure inside the mask is less than atmospheric pressure.

Figure 15A:
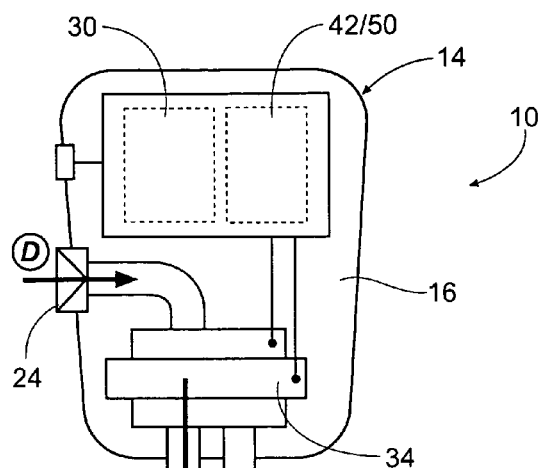
FIGS. 15A and 15B are schematic views a self-contained, intermittent positive airway pressure system as shown in FIGS. 1A to 1D or FIGS. 2A and 2B, which includes a positive pressure source comprising a turbine 34 (or a blower 36) and dual purpose valve A/B, FIG. 15A showing the system during inhalation and FIG. 15B showing the system during exhalation.
Figure 15A:
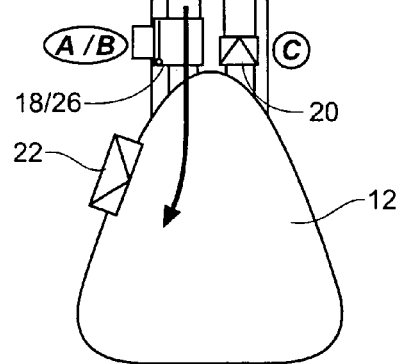
Figure 15B:
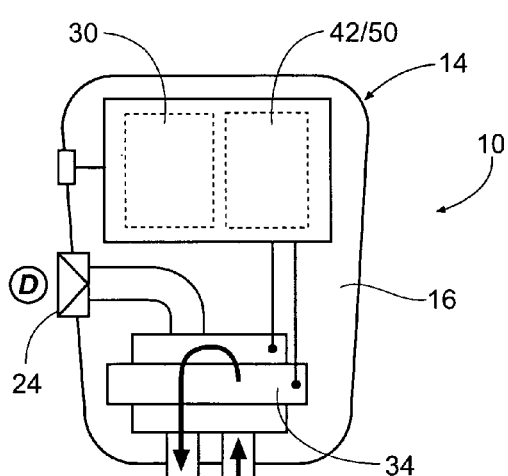
Figure 15B:
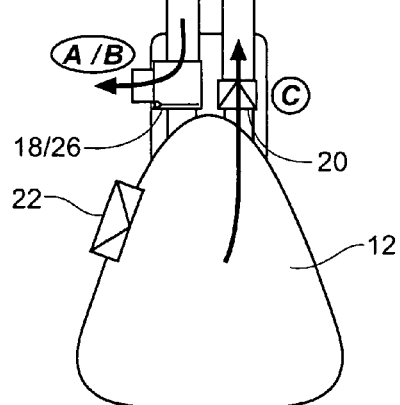

As shown in FIGS. 15A and 15B, the mask inlet valve (A) and the ambient air outlet valve 26 (B) can be combined to comprise a single a dual purpose valve (designated A/B). The dual purpose valve (A/B) has only two positions: (i) mask inlet valve 18-(A) opened and ambient air outlet valve 26 (B) closed, as shown in FIG. 15A; or (ii) mask inlet valve 18 (A) closed and ambient air outlet valve 26 (B) opened, as FIG. 15B shows.

Upon inhalation by the user, dual purpose valve (A/B) switches such that the mask inlet valve 18 (A) is opened and the ambient air outlet valve 26 (B) is closed, as shown in FIG. 15A. Simultaneously, the mask outlet valve 20 (C) is pulled closed by the lower pressure. Ambient air inlet valve 24 (D) opens from the lower pressure to allow fresh air in from the atmosphere. At a predetermined or calculated time (calculated by detection of change in pressure, turbine 34 speed, or valve position), the power assisted turbine 34 or blower 36 sequence is initiated to provide additional pressure before and/or during inhalation, sufficient to resist tissue collapse in the upper airway.

Upon initiation of exhalation by the user, the dual purpose valve (A/B) switches such that the mask inlet valve 18 (A) is closed and the ambient air outlet valve 26 (B) is opened, as shown in FIG. 15B. The mask outlet valve 20 (C) is opened by the high pressure created by the user. The ambient air inlet valve 24 (D) is closed by the higher pressure. Air exits the user's mask 12 through the mask outlet valve 20 (C) and into the turbine 34 (if present). Now the turbine 34 provides resistance to the user's expiration, to aid in keeping the user's airway open during exhalation due to the increased air pressure. Exhaled air escapes to atmosphere after passing through the turbine 34 through the ambient air outlet valve 26 (B). During this phase the turbine 34 may be used to collect and store energy provided by the user. In this configuration, the dual purpose valve AB could provide the optimal place for a sensor, as will be described.

7. Sensors

As FIGS. 13A to 13D show, the various embodiments of the airflow regulation assembly 14 previously described can include one or more sensors $S_N$ communicating with the components of the airflow regulation assembly 14 to sense current conditions that relate to the respiratory cycle. The sensors $S_N$ can comprise various mechanical, and/or chemical, and/or temperature, and/or electrical sensing devices. FIGS. 13A to 13D show candidate positions for the sensors $S_N$.

Figure 13A:
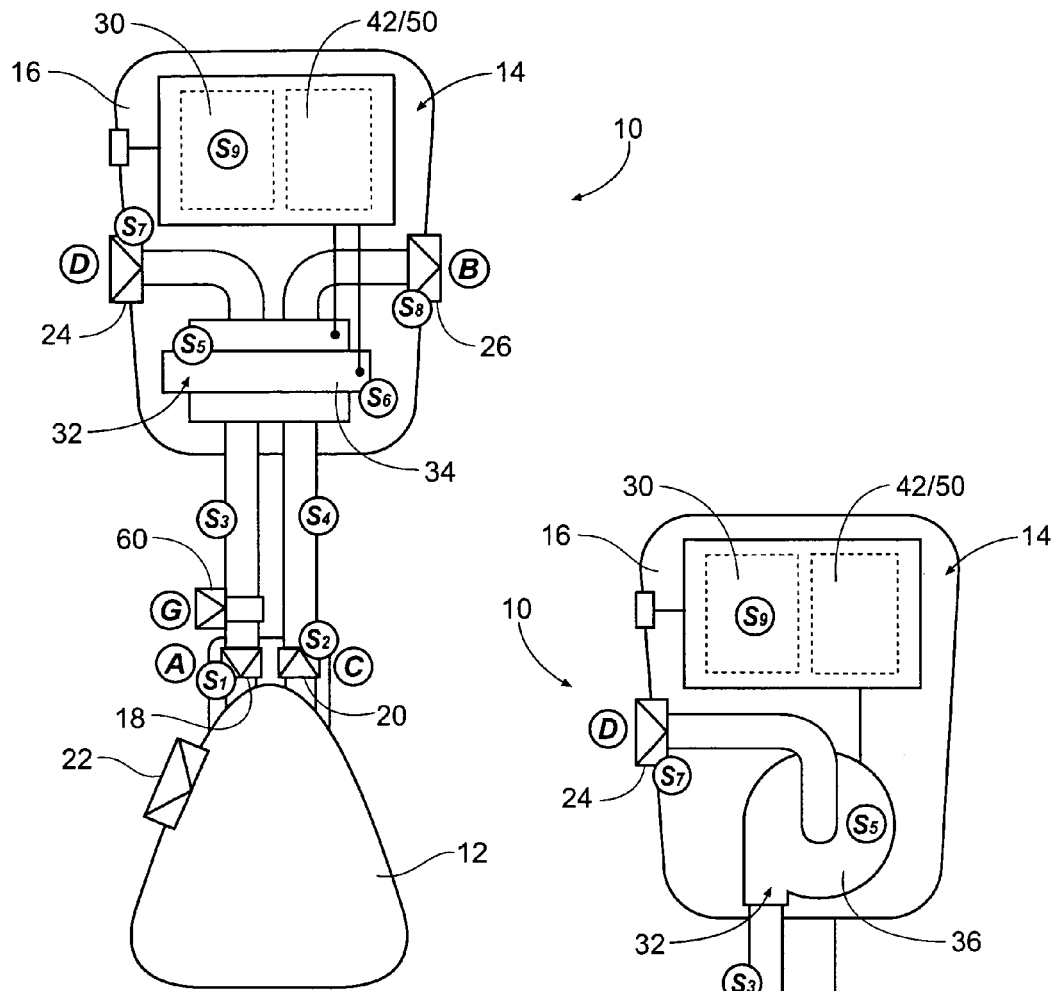
FIGS. 13A to 13D are schematic views showing representative self-contained, intermittent positive airway pressure systems as shown in FIGS. 4A/B, 6A/6B, 8A/8B, and 9A/9B, and further showing candidate locations for sensors to aid in the functionality of the systems.
Figure 13B:
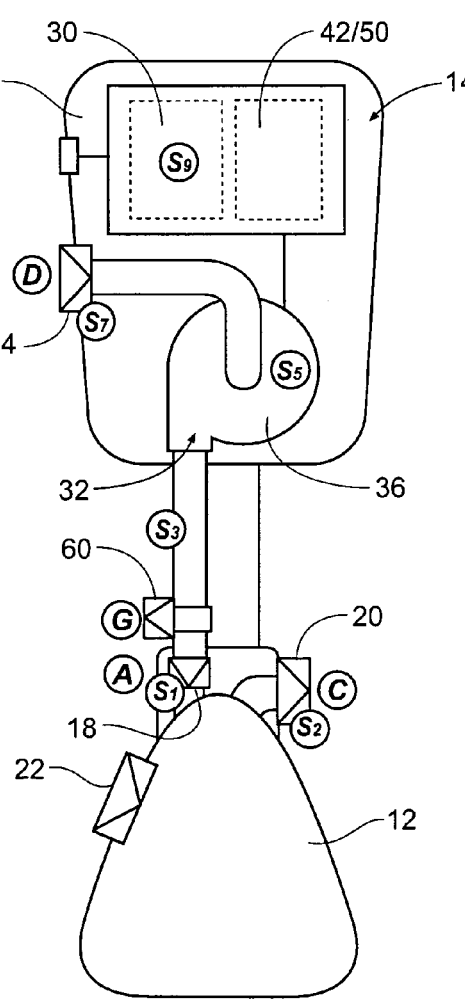
Figures 13C, 13D:
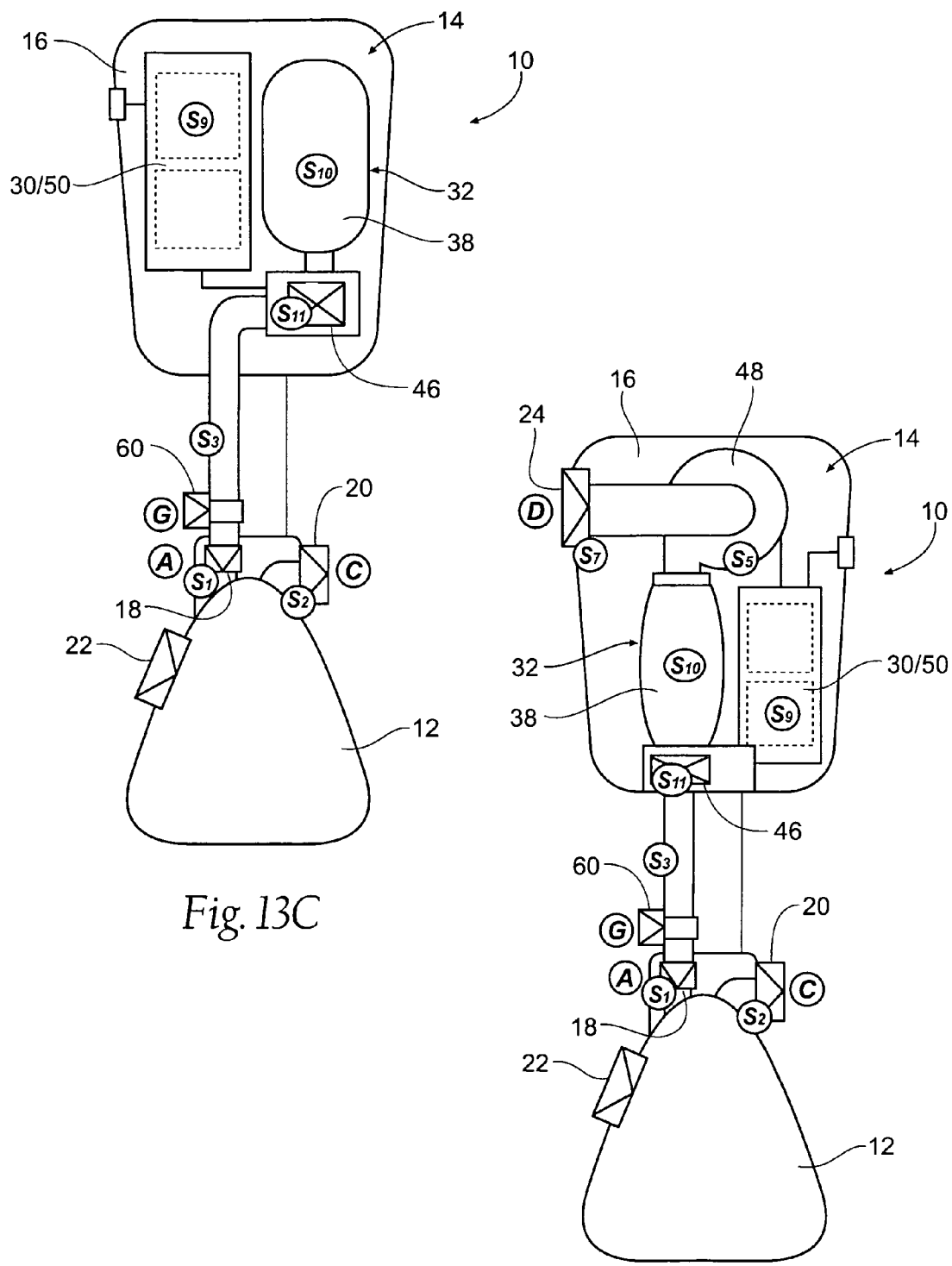

FIG. 13A shows candidate positions for sensors $S_N$ in a turbine 34 configuration like that shown in FIGS. 4A/B. FIG. 13B shows candidate positions for sensors $S_N$ in a blower 36 configuration like that shown in FIGS. 6A/B. FIG. 13C shows candidate positions for sensors $S_N$ in an air reservoir configuration like that shown in FIGS. 8A/B. FIG. 13D shows candidate positions for sensors $S_N$ in a blower 36-air reservoir configuration like that shown in FIGS. 9A/B.

The sensors $S_N$ can be conditioned to sense various pressure, flow, and temperature conditions relating to the respiratory cycle, e.g., change in air pressure at various locations within the manifold 16 or airflow velocity at various locations within the manifold 16 (e.g., in FIGS. 13A to 13D, $S_3$ and $S_4$); the speed of rotation of the turbine 34/blower 36 (e.g., in FIGS. 13A to 13D, $S_5$); valve conditions (open or closed) e.g., in FIGS. 13A to 13D, $S_1$, $S_2$, $S_7$, $S_8$, $S_{11}$); air reservoir pressure (if present) (e.g., in FIGS. 13A to 13D, $S_{10}$); generator output ((e.g., in FIGS. 13A to 13D, $S_6$); amount of stored energy (e.g., in FIGS. 13A to 13D, $S_9$); and/or temperature/humidity/pressure/flow conditions at various locations within the manifold 16 (e.g., in FIGS. 13A to 13D, $S_3$ and $S_4$).

In this arrangement (see FIGS. 13A to 13D), the airflow regulation assembly 14 desirably includes a controller or processing element 30, such as an on-board integrated circuit or simple computer. The processing element 30 desirably includes preprogrammed rules or algorithms for processing the sensed output(s) of the sensors and providing commands to the components of the airflow regulation assembly 14 to optimize their intended function.

For example, based upon the output of the sensors, the processing element 30 can directly determine the drop of expiration pressure toward the end of the exhalation phase. The processing element 30 can generate, in response to this sensed condition, a command that initiates powering up of the turbine 34/blower 36 (or the opening of the valve(s) communicating with the air reservoirs 38) to provide positive pressure to increase native pressure in the airway sufficient to resist tissue collapse in the upper airway at or slightly before initiation of the inspiration phase, thereby proactively preventing the collapse of the airway. Upon sensing the rise of expiration pressure toward the beginning of the exhalation phase, the processing element can, in response, generate a command that terminates operation of the turbine 34/blower 36 (or closes the valve(s) communicating with the air reservoirs 38). Using the sensors and processing element, the airflow regulation assembly 14 provides positive air pressure sufficient to resist tissue collapse in the upper airway intermittently during only a portion of the respiratory cycle.

The processing element 30 can also include preprogrammed rules that predict, based upon the sensed conditions, the likely onset of tissue collapse that could lead to an apnea or a hypopnea. For example, sensed conditions can indicate that an airway blockage has occurred or is likely to occur. In this arrangement, the processing element can generate a command that initiates powering up of the turbine 34/blower 36 to provide positive pressure to augment ambient pressure in the airway sufficient to resist tissue collapse in the upper airway when such conditions occur or are likely to occur.

Even people who are severely affected by sleep apnea only have apneas or hypopneas in only a small percentage of respiratory cycles. A person with an AHI of 30 experiences a blockage, on average, once every two minutes. This is approximately 5% of breathes. The presence of sensors and the processing element that detect or predict an oncoming apnea or hypopnea or the likelihood of an apnea or hypopnea makes possible the generation of a command that initiates powering up of the turbine 34/blower 36 (or the opening of the valve(s) communicating with the air reservoirs 38) to provide positive pressure to augment native pressure in the airway sufficient to resist tissue collapse in the upper airway only when such conditions occur or are deemed likely to occur. During the other respiratory cycles, air can enter the mask 12 through the one way valves during inhalation without activation of the positive pressure source.

The presence of a processing element 30 with pre-programmable rules makes possible an airflow regulation assembly 14 having multiple functioning modes. In one mode, the airflow regulation assembly 14 provides air pressure assistance sufficient to resist tissue collapse in the upper airway on each inhalation. In another mode, the airflow regulation assembly 14 provides air pressure assistance sufficient to resist tissue collapse in the upper airway only when a blockage or narrowing event is detected or is deemed likely. In another mode, the airflow regulation assembly 14 provides assistance sufficient to resist tissue collapse in the upper airway during some, but not all inhalations, e.g., during every third inhalation. The presence of a processing element with pre-programmable rules makes possible an airflow regulation assembly 14 that can be optimized for the need of individual users sufficient to resist tissue collapse in the upper airway.

8. Condensation and Humidity Regulation

Desirably, condensation and humidity levels are regulated in the mask 12. Humidity regulation can help prevent discomfort created by the drying out of the air passage throughout the night. However, in the moist interior of the mask 12, liquid will condense on the plastic and other surfaces which are cooler, and can then drip or run onto the user causing another sleep disturbance.

With the regulation of condensation and humidity levels in the mask 12 in mind, the self-contained, intermittent positive airway pressure system 10 desirably comprises materials that function well in moist environments, and adjust to changing temperature rapidly to avoid condensation surfaces. The self-contained, intermittent positive airway pressure system 10 also desirably comprises a geometry that limits the number of condensation surfaces and provides designated outflow channels for the escape of condensed fluids without disturbing the user. Additionally, the condensed fluids could be recycled within the system 10 to ensure that the inhaled air is adequately humid.

Furthermore, airflow regulation assembly 14 can include a small reservoir 62 (see FIG. 3) for water to provide added humidity throughout the night. This fluid could be held in a sponge or similar such absorbent material in the manifold 16. The absorbent material could gather the exhaled condensation and use it to provide humidity for the inhaled air.

We claim:

1. A system to aid respiration of an individual during a respiratory cycle having an inhalation phase and an exhalation phase comprising an air flow director sized and configured to be worn in or over the nose of the individual in communication with an upper airway, and an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle, wherein the source of positive pressure includes a turbine, and wherein, during at least a portion of the second mode, the turbine rotates in response to exhalation airflow through the turbine to resist exhalation airflow.

2. A system according to claim 1 wherein the controller includes at least one sensor communicating with the airflow regulation assembly to sense at least one condition relating to the respiratory cycle.

3. A system according to claim 1 wherein the controller includes at least one sensor communicating with the airflow regulation assembly to sense at least one condition relating to operation of the airflow regulatory assembly.

4. A system according to claim 1 wherein the controller includes at least one sensor communicating with the airflow regulation assembly to sense at least one condition relating to the respiratory cycle, and wherein the controller includes a processing element including preprogrammed rules that predict, based upon at least one sensed condition, the likely onset of tissue collapse in the upper airway.

5. A system according to claim 1 wherein, during at least a portion of the first mode, the controller operates the source of positive pressure to increase positive air pressure in the air flow director sufficient to resist tissue collapse in the upper airway.

6. A system according to claim 1 wherein, during at least a portion of the second mode, the controller operates the source of positive pressure to increase positive air pressure in the air flow director sufficient to resist tissue collapse in the upper airway.

7. A system according to claim 1 wherein, during at least a portion of the first mode, the controller operates the turbine to convey positive air pressure into the air flow director sufficient to resist tissue collapse in the upper airway.

8. A system according to claim 1 wherein, during at least a portion of the second mode, the controller operates the turbine to convey positive air pressure into the air flow director sufficient to resist tissue collapse in the upper airway.

9. A system according to claim 1 wherein the turbine includes a generator to generate energy as the turbine rotates in response to exhalation airflow.

10. A system according to claim 9 wherein the airflow regulation assembly includes an energy storage element coupled to the generator.

11. A system according to claim 10 wherein, during at least a portion of the first mode, the controller directs energy from the energy storage element to operate the turbine to convey positive air pressure into the air flow director sufficient to resist tissue collapse in the upper airway.

12. A system according to claim 1 wherein the air flow director includes means for restricting airflow during exhalation.

13. A system according to claim 12 wherein the means includes an array of exhaled air ports.

14. A system to aid respiration of an individual during a respiratory cycle having an inhalation phase and an exhalation phase comprising an air flow director sized and configured to be worn in or over the nose of the individual in communication with an upper airway, and an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle, wherein the source of positive pressure includes a blower; and wherein the airflow regulation assembly includes a turbine that, during the second mode, rotates in response to exhalation airflow through the turbine to resist exhalation airflow.

15. A system according to claim 14
wherein, during at least a portion of the first mode, the controller operates the blower to convey positive air pressure into the air flow director sufficient to resist tissue collapse in the upper airway.

16. A system according to claim 14
wherein, during at least a portion of the second mode, the controller operates the blower to convey positive air pressure into the air flow director sufficient to resist tissue collapse in the upper airway.

17. A system according to claim 14
wherein the turbine includes a generator to generate energy as the turbine rotates in response to exhalation airflow.

18. A system according to claim 17
wherein the airflow regulation assembly includes an energy storage element coupled to the generator.

19. A system according to claim 18
wherein, during at least a portion of the first mode, the controller directs energy from the energy storage element to operate the blower to convey positive air pressure into the air flow director sufficient to resist tissue collapse in the upper airway.

20. A system to aid respiration of an individual during a respiratory cycle having an inhalation phase and an exhalation phase comprising
an air flow director sized and configured to be worn in or over the nose of the individual in communication with an upper airway, and
an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle,
wherein the source of positive pressure includes an reservoir of air subject to a positive pressure, and
wherein, during at least a portion of the first mode, the controller opens the reservoir to convey positive air pressure into the air flow director sufficient to resist tissue collapse in the upper airway.

21. A system to aid respiration of an individual during a respiratory cycle having an inhalation phase and an exhalation phase comprising
an air flow director sized and configured to be worn in or over the nose of the individual in communication with an upper airway, and
an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle,
wherein the source of positive pressure includes an reservoir of air subject to a positive pressure, and
wherein, during at least a portion of the second mode, the controller opens the reservoir to convey positive air pressure into the air flow director sufficient to resist tissue collapse in the upper airway.

22. A system to aid respiration of an individual during a respiratory cycle having an inhalation phase and an exhalation phase comprising
an air flow director sized and configured to be worn in or over the nose of the individual in communication with an upper airway, and
an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle,
wherein the source of positive pressure includes an reservoir of air subject to a positive pressure, and
wherein the airflow regulation assembly includes a turbine that, during the second mode, rotates in response to exhalation airflow through the turbine to resist exhalation airflow.

23. A system to aid respiration of an individual during a respiratory cycle having an inhalation phase and an exhalation phase comprising
an air flow director sized and configured to be worn in or over the nose of the individual in communication with an upper airway, and
an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle,
wherein the source of positive pressure includes an reservoir of air subject to a positive pressure, and
wherein the reservoir includes a pre-charged air canister insertable into and out of the airflow regulation assembly.

24. A system to aid respiration of an individual during a respiratory cycle having an inhalation phase and an exhalation phase comprising an air flow director sized and configured to be worn in or over the nose of the individual in communication with an upper airway, and an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle, wherein the source of positive pressure includes an reservoir of air subject to a positive pressure, and wherein the reservoir includes a bladder, and wherein the airflow regulation assembly includes a blower to charge the bladder with positive air pressure.

25. A system to aid respiration of an individual during a respiratory cycle having an inhalation phase and an exhalation phase comprising an air flow director sized and configured to be worn in or over the nose of the individual in communication with an upper airway, and an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle, wherein the airflow regulation assembly includes a source of power for operating the source of positive pressure, wherein the source of power comprises a rechargeable energy storage element, wherein the airflow regulation assembly includes a turbine that, during the second mode, rotates in response to exhalation airflow through the turbine to resist exhalation airflow, the turbine including a generator to generate energy as the turbine rotates in response to exhalation airflow, wherein the rechargeable energy storage element is coupled to the generator, and wherein the controller directs energy from the energy storage element to operate the source of positive pressure to convey positive air pressure into the air flow director sufficient to resist tissue collapse in the upper airway.

26. A system according to claim 25
wherein the source of power comprises a battery.

27. A system to aid respiration of an individual during a respiratory cycle having an inhalation phase and an exhalation phase comprising an air flow director sized and configured to be worn in or over the nose of the individual in communication with an upper airway, and an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle, wherein the air flow director includes means for restricting airflow during exhalation, wherein the means includes an array of exhaled air ports, and wherein the flow area of the exhaled air ports is adjustable.

28. A system to aid respiration of an individual during a respiratory cycle having an inhalation phase and an exhalation phase comprising an air flow director sized and configured to be worn in or over the nose of the individual in communication with an upper airway, and an airflow regulation assembly sized and configured to be worn in its entirety by the individual in communication with the air flow director and operative in a first mode to regulate the supply of air to the air flow director during the inhalation phase of the respiratory cycle and in a second mode to regulate the exhaust of air from the air flow director during the exhalation phase of the respiratory cycle, the airflow regulation assembly including a source of positive pressure and a controller to intermittently operate the source of positive pressure to increase positive air pressure in the air flow director sufficient to resist tissue collapse in the upper airway during only a portion of the respiratory cycle less than the entire respiratory cycle, wherein the air flow director includes means for restricting airflow during exhalation, and wherein the means includes a turbine that rotates in response to exhalation airflow through the turbine to resist exhalation airflow.

* * * * *